United States Patent
C.-Gaudreault et al.

(10) Patent No.: US 9,579,306 B2
(45) Date of Patent: *Feb. 28, 2017

(54) SUBSTITUTED 2-IMIDAZOLIDINONES AND 2-IMIDAZOLONES AND THEIR USE IN THE TREATMENT OF CANCER

(71) Applicant: UNIVERSITÉ LAVAL, Québec (Québec) (CA)

(72) Inventors: René C.-Gaudreault, Berniéres (CA); Sébastien Fortin, St-Etienne-de-Lauzon (CA)

(73) Assignee: UNIVERSITE LAVAL, Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/061,439

(22) Filed: Mar. 4, 2016

(65) Prior Publication Data

US 2016/0184270 A1    Jun. 30, 2016

Related U.S. Application Data

(62) Division of application No. 14/239,150, filed as application No. PCT/CA2012/000751 on Aug. 10, 2012, now Pat. No. 9,278,937.

(60) Provisional application No. 61/523,999, filed on Aug. 16, 2011.

(51) Int. Cl.
| | | |
|---|---|---|
| A61K 31/4166 | (2006.01) |
| A61K 31/635 | (2006.01) |
| C07D 233/36 | (2006.01) |
| C07D 233/32 | (2006.01) |

(52) U.S. Cl.
CPC ......... *A61K 31/4166* (2013.01); *A61K 31/635* (2013.01); *C07D 233/32* (2013.01); *C07D 233/36* (2013.01)

(58) Field of Classification Search
CPC combination set(s) only.
See application file for complete search history.

(56) References Cited

U.S. PATENT DOCUMENTS

| | | |
|---|---|---|
| 4,279,637 A | 7/1981 | Wu |
| 5,541,197 A | 7/1996 | Fisher et al. |
| 5,705,515 A | 1/1998 | Fisher et al. |
| 2012/0309777 A1 | 12/2012 | Gaudreault et al. |

FOREIGN PATENT DOCUMENTS

| | | |
|---|---|---|
| EP | 1621535 A1 | 2/2006 |
| WO | 99/44609 A1 | 9/1999 |
| WO | 01/02350 A2 | 1/2001 |
| WO | 03/014113 A1 | 2/2003 |
| WO | 2005/004810 A2 | 1/2005 |

OTHER PUBLICATIONS

Naylor et al. "Human Beta-3 Adrenergic Receptor Agonists Containing Imidazolidinone and Imidazolone Benzenesulfonamides" Bioorg. Med. Chem. Lett. 1999, 9, 755-758.*
Fortin et al. "Design, Synthesis, Biological Evaluation, and Structure-Activity Relationships of Substituted Phenyl 4-(2-Oxoimidazolidin-1-yl)-benzenesulfonates as New Tubulin Inhibitors Mimicking Combretastatin A-4" J. Med. Chem. 2011, 54, 4559-4580.*
Fortin et al., 2011, "Design, Synthesis, Biological Evaluation, and Structure-Activity Relationships of Substituted Phenyl 4-(2-Oxoimidazolidin-1-yl)-benzenesulfonates as New Tubulin Inhibitors Mimicking Combretastatin A-4," J. Med. Chem., 54:4559-4580.
Fortin et al., 2011, "Substituted Phenyl 4-(2-Oxoimidazolidin-1-yl)benzenesulfonamides as Antimitotics, Antiproliferative, Antiangiogenic and Antitumoral Activity, and Quantitative Structure-Activity Relationships," European Journal of Medicinal Chemistry, 46:5327-5342.
Naylor et al., 1999, "Human Beta-3 Adrenergic Receptor Agonists Containing Imidazolidinone and Imidazolone Benzenesulfonamids," Bioorganic & Medicinal Chemistry Letters, 9:755-758.
Parmee et al., 1999, "Human Beta-3 Adrenergic Receptor Agonists Containing Cyclic Ureidobenzenesulfonamides," Bioorganic & Medicinal Chemistry Letters, 9:749-754.
Turcotte et al., 2012, "Synthesis, Biological Evaluation, and Structure-Activity Relationships of Novel Substituted N-Phenyl Ureidobenzenesulfonate Derivatives Blocking Cell Cycle Progression in S-Phase and Inducing DNA Double-Strand Breaks," J. Med. Chem., 55:6194-6208.
PCT International Search Report for PCT Application No. PCT/CA2012/000751 mailed Nov. 5, 2012 (7 pages).

* cited by examiner

*Primary Examiner* — Joseph Kosack
*Assistant Examiner* — Amanda L Aguirre
(74) *Attorney, Agent, or Firm* — Sutherland Asbill & Brennan LLP

(57) ABSTRACT

Compounds of formula (I) wherein $R_1$, $R_4$, $R_8$, X and Y as defined herein are provided as useful for the inhibition of certain types of cancer cells, amongst others, breast cancer cells, or for the manufacture of anti-cancer agents.

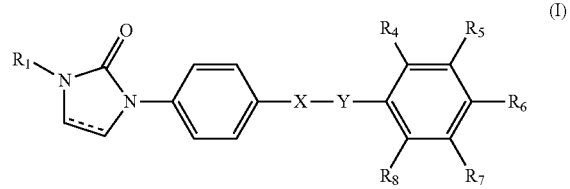

11 Claims, No Drawings

SUBSTITUTED 2-IMIDAZOLIDINONES AND 2-IMIDAZOLONES AND THEIR USE IN THE TREATMENT OF CANCER

CROSS REFERENCE TO RELATED APPLICATIONS

This application is a divisional of U.S. application Ser. No. 14/239,150, filed Jun. 6, 2014, now U.S. Pat. No. 9,278,937, which claims the priority benefit of PCT/CA2012/000751 filed on Aug. 10, 2012, and U.S. Provisional Application No. 61/523,999 filed on Aug. 16, 2011. The contents of these applications are hereby incorporated by reference in their entireties.

FIELD OF THE INVENTION

The present invention relates to substituted 2-imidazolidones having selective activity against certain types of cancer cells. Particularly, these compounds are useful as anti-cancer agents. Still, the invention relates to the use of these compounds for the manufacture of anti-cancer agents and method of treating certain types of cancer, amongst others, gastrointestinal and breast cancer and metastasis with these compounds. The invention also relates to processes for the preparation of these compounds.

BACKGROUND OF THE INVENTION

Cancer is a disease that seriously jeopardizes the health of human beings. Around the globe, about 6 millions people die of cancer every year, with another 10 millions seriously affected by the disease. According to the estimate of the World Health Organization, in the 21st century, cancer will become the "number one killer" of mankind.

In the past several decades, many ways of treating cancer became available, mainly including surgery, radiotherapy, chemotherapy, hormonotherapy, gene therapy, and immunotherapy, among which surgery, radiotherapy and chemotherapy have become the major means. Chemotherapy refers to treating cancer with chemical medication. It is the most rapidly expanding field in the diagnosis and treatment of cancer. A great number of new medicines aiming at different targets are ready for clinical application, and developments in research in mechanism of drug action and pharmacokinetics have made the clinical administration routes and means more fitting for killing tumor cells while protecting the normal tissues.

At present, pharmaceuticals for chemotherapy mainly includes: compounds that affects the biosynthesis of nucleic acid (e.g., 5-fluorouracil, amethopterin, cytarabine, hydroxyurea); compounds that directly destroys DNA and prevents its reproduction, e.g. alkylating agents (e.g., cisplatin and carboplatin); antineoplastic antibiotics (e.g., daunorubicin, mitomycin C) compounds that interferes with the transcription and prevents the synthesis of RNA (e.g., actinomycin D, adriamycin) and other transcription restraining antibiotics; compounds that affects the synthesis of protein (e.g., catharanthines, podophyllotoxins, asparaginase) hormones (e.g., adrenal cortical hormone, estrogen, androgen, tamoxifen, aminoglutethimide). The property of interfering in the polymerization or depolymerization of microtubulin of many natural medicines is regarded as having antineoplastic activity. Historically, research focused on two classes of antimitotic agents. The first class includes compounds that bind reversibly to tubulin and prevent microtubule assembly (e.g., colchicine, vinblastine, combretastatin). The second class of antimicrotubule agents features molecules that prevent microtubule disassembly (e.g., taxotere, epothilone, discodermolide, eleutherobine).

Despite the utility of taxus and vinca alkaloids in the clinic, there are serious limitations to these therapies. On-target toxicity of these agents is associated with the notion that tubulin polymers play a critical role in the non-mitotic cytoskeletal functions in both proliferating and terminally differentiated cells. Microtubules are also essential for axonal transport in neurons. Peripheral neurotoxicity of Paclitaxel™, Docetaxel™ and Vincristine™ has been extensively studied. Although manageable and reversible for the majority of second-generation anti-mitotic drugs, this severe side effect may preclude repeated courses of therapy. Neuropathy continues to be an issue for novel agents in clinical development, for example dolastatin-10. In addition, drug efflux pumps play a role in tumors developing resistance to the tubulin-binding drugs. For example, vinca alkaloids and taxanes are both substrates for the P-gp efflux pump encoded by the multidrug resistance mdr1 gene, resulting in decreased sensitivity to these compounds in vivo. Due to these limitations of the tubulin-binding antimitotic agents, there is ongoing need to identify new subsets of antimicrotubule agents that yield anti-mitotic effect with better specificity and more predictable pharmacology One major drawback when treating cancer is to achieve selectivity against this type of cancer cells. Most chemotherapy against these types of cancer comprises: anti-estrogen therapy such as tamoxifene, raloxifene and toremifene that are Selective Estrogen Receptor Modulators (SERM) that block estrogen's action on some tissues or organs and acts like estrogen on others. They are used for both pre- and postmenopausal women and considered as the first-line hormone therapy. In addition, there is also fulvestrant that is a pure estrogen receptor antagonist.

Selective aromatase inhibitors such as letrozole, anastrozole and exemestane, and nonselective aromatase inhibitors such as aminoglutethimide and testolactone are blocking the function of the enzyme aromatase, which is needed to convert pre-estrogen into a biologically active form. These molecules block the conversion of a pre-estrogen compound produced by tissues other than the ovaries into estrogen. They are used also in the first- and the second-line therapy for early stage breast cancer as well as for postmenopausal women. In the third-line therapy are found progesterone-like drugs such as megestrol acetate. These drugs are traditionally used in postmenopausal women after tamoxifen no longer works. Finally, there are the Luteinizing Hormone-Releasing Hormone (LHRH)-like drugs such as goserelin and leuprolide acetate that reduce estrogen production by the ovaries and used in premenauposal women in complement with aromatase inhibitors.

There remains a need to discover and synthesize new potent compounds having selective activity against certain types of cancer cells, there by providing highly selective anti-cancer molecules.

Certain substituted 2-imidazolidones have now been found to be specific for certain types of cancer cells.

SUMMARY OF THE INVENTION

In one aspect of the present invention, there is provided a compound of formula (I):

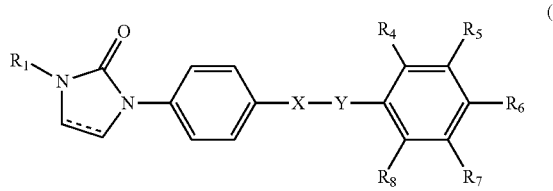

(I)

wherein:

imidazo ring is saturated or unsaturated;

$R_1$ is $C_{3-8}$ linear or branched alkyl provided that α-carbon of said alkyl (i.e. that is adjacent to the nitrogen of imidazo ring) is unsubstituted;

X is O or NH when $Y=SO_2$; and $X=SO_2$ when Y is O or NH;

or X is —CH=CH— and Y is C=O;

or X is C=O, —S— or C=CH$_2$; and Y is absent;

$R_4$ and $R_8$ is each independently selected from the group consisting of: H, OH, halogen, $C_{1-6}$ alkyl and $C_{1-6}$ alkoxy;

$R_5$, $R_6$ and $R_7$ is each independently selected from the group consisting of: H, OH, halogen, $C_{1-6}$ alkyl and $C_{1-6}$ alkoxy, provided that at least one of $R_4$, $R_5$, $R_6$, $R_7$ or $R_8$ is substituted;

or a pharmaceutically acceptable derivative or salt thereof.

In one aspect of the present invention, there is provided a compound of formula (I):

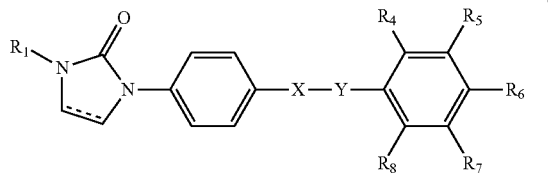

(I)

wherein:

imidazo ring is saturated or unsaturated;

$R_1$ is n-propyl, n-butyl, isobutyl, n-pentyl, isopentyl, 2,2-dimethylbutyl or n-hexyl;

X is O or NH when $Y=SO_2$; and $X=SO_2$ when Y is O or NH;

or X is —CH=CH— and Y is C=O;

or X is C=O, —S— or C=CH$_2$; and Y is absent;

$R_4$ and $R_8$ is each independently selected from the group consisting of: H, OH, halogen, $C_{1-6}$ alkyl and $C_{1-6}$ alkoxy;

$R_5$, $R_6$ and $R_7$ is each independently selected from the group consisting of: H, OH, halogen, $C_{1-6}$ alkyl and $C_{1-6}$ alkoxy, provided that at least one of $R_4$, $R_5$, $R_6$, $R_7$ or $R_8$ is substituted;

or a pharmaceutically acceptable derivative or salt thereof.

In a particular embodiment of the present invention, there is provided a compound of formula (Ia):

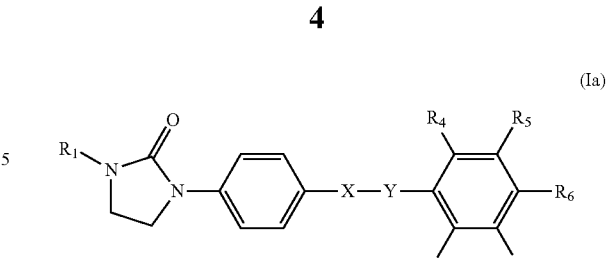

(Ia)

$R_1$ is n-propyl, n-butyl, isobutyl, n-pentyl, isopentyl, 2,2-dimethylbutyl or n-hexyl;

X is O or NH when $Y=SO_2$; and $X=SO_2$ when Y is O or NH;

$R_4$ and $R_8$ is each independently selected from the group consisting of: H, OH, halogen, $C_{1-4}$ alkyl and $C_{1-6}$ alkoxy;

$R_5$, $R_6$ and $R_7$ is each independently selected from the group consisting of: H, OH, halogen, $C_{1-4}$ alkyl and $C_{1-4}$ alkoxy, provided that at least one of $R_4$, $R_5$, $R_6$, $R_7$ or $R_8$ is substituted;

or a pharmaceutically acceptable derivative or salt thereof.

In a particular embodiment of the present invention, there is provided a compound of formula (Ia), wherein:

$R_1$ is n-propyl, n-butyl, isobutyl or n-pentyl, isopentyl or n-hexyl;

$X=SO_2$ when Y is O or NH;

$R_4$ and $R_8$ are H;

$R_5$, $R_6$ and $R_7$ is each independently selected from the group consisting of: H, halogen and $C_{1-3}$ alkoxy, provided that at least one of $R_4$, $R_5$, $R_6$, $R_7$ or $R_8$ is substituted;

or a pharmaceutically acceptable salt thereof.

In a particular embodiment of the present invention, there is provided a compound of formula (Ia), wherein $R_1$ is n-propyl, n-butyl, isobutyl or n-pentyl; X is O or NH when $Y=SO_2$; and $X=SO_2$ when Y is O or NH; $R_4$ is H and $R_8$ is H; $R_5$, $R_6$ and $R_7$ is each independently selected from the group consisting of: H, halo, and $C_{1-3}$ alkoxy, provided that at least one of $R_5$, $R_6$ and $R_7$ is not H, or a pharmaceutically acceptable salt thereof.

In a particular embodiment of the present invention, there is provided a compound of formula (Ia), wherein $R_1$ is n-propyl, n-butyl, isobutyl or n-pentyl; $X=SO_2$ and Y is O or NH; $R_4$ is H and $R_8$ is H; $R_5$, $R_6$ and $R_7$ is each independently selected from the group consisting of: H, halo, and OMe, provided that at least one of $R_5$, $R_6$ and $R_7$ is not H, or a pharmaceutically acceptable salt thereof.

A second aspect of the present invention is directed to pharmaceutical compositions comprising at least one compound of Formula (I) or (Ia), or a salt thereof, and one or more pharmaceutically-acceptable excipients.

A further aspect of the present invention is directed to a method of treating a condition that results from abnormal cell growth, cellular differentiation, tumor growth or invasion with one or more compounds of Formula (I) or (Ia).

A further aspect of the invention is directed to a method of treating cancer or a metastasis thereof in a human suffering therefrom, particularly wherein the cancer is gastrointestinal or breast cancer comprising administering a therapeutically effective amount of a compound of Formula (I) or (Ia).

A further aspect of the invention is directed to the use of one or more compounds of formula (I) or (Ia) for the manufacture of medicament for the treatment of a cancer or a metastasis thereof in a human, particularly wherein the cancer is gastrointestinal or breast cancer.

A further aspect of the invention is directed to hindering or blocking cell cycle progression by contacting one or more cells with one or more compounds of Formula (I) or (Ia).

A further aspect of the present invention is directed to a method of synthesizing compounds of Formula (I) or (Ia) by following one or more synthetic schemes as defined below.

The compounds of Formula (I) or (Ia) may also be solvated, especially hydrated. Hydration may occur during manufacturing of the compounds or compositions comprising the compounds, or the hydration may occur over time due to the hygroscopic nature of the compounds.

When any variable occurs more than one time in any constituent of Formula (I) or (Ia), its definition on each occurrence is independent of its definition at every other occurrence. Also, combinations of substituents and/or variables are permissible only if such combinations result in stable compounds.

The invention disclosed herein is also meant to encompass the in vivo metabolic products of the disclosed compounds. Such products may result, for example, from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabeled compound of the invention, administering it parenterally or enterally in a detectable dose to an animal such as rat, mouse, guinea pig, monkey, or to human, allowing sufficient time for metabolism to occur and isolating its conversion products from the urine, blood or other biological samples.

The invention disclosed herein is also meant to encompass pro-drugs that, when administered in vivo, provide the compounds of formula (I) or (Ia) as metabolic products. Such products may result, for example, from the addition of phosphate, boronic acid or amino acid derivatives. Accordingly, the invention includes compounds of formula (I) or (Ia) wherein appropriate $R_4$, $R_5$, $R_6$, $R_7$ or $R_8$ is derivatized with a phosphate, a boronic acid or an amino acid, or a salt thereof.

Some of the compounds disclosed herein may contain one or more asymmetric centers and thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

DETAILED DESCRIPTION OF THE INVENTION

Definitions

The term "$C_{1-n}$alkyl" such as "$C_{1-8}$alkyl" as employed herein by itself or as part of another group refers to both straight and branched chain radicals, and unless otherwise specified up to n carbons, such as for example $C_{1-8}$ alkyl: methyl, ethyl, propyl, isopropyl, n-butyl, s-butyl, t-butyl, isobutyl, pentyl, hexyl, isohexyl, heptyl, 4,4-dimethylpentyl, octyl, 2-2-dimethylbutyl and 2,2,4-trimethylpentyl.

The term "alkoxy" or "alkyloxy" refers to any of the above alkyl groups linked to an oxygen atom. Typical examples are methoxy, ethoxy, isopropyloxy, sec-butyloxy, and t-butyloxy.

The term "halogen" or "halo" as employed herein by itself or as part of another group refers to chlorine, bromine, fluorine or iodine.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The term "enantiomeric excess" refers to a mixture wherein one enantiomer is present in a greater concentration than its mirror image molecule.

The term "selective" or "selectivity" refers to the activity of a compound against a certain cell line or against a certain type of cancer that is qualified as sensitive relative to the activity of that same compound against another type of cell line or another type of cancer that is characterized as non-sensitive. The compound is determined or deemed "selective" if the activity against the sensitive cell line is reproducibly greater (i.e. lower $GI_{50}$ or $IC_{50}$) and the activity against the non-sensitive cell line. For example, a compound is deemed selective if its activity against the sensitive cells is at least twice the activity (or the $GI_{50}$ is half) of the non-sensitive cells. The ratio is expressed as the ratio of $GI_{50}$ non-sensitive cells over $GI_{50}$ sensitive cells. Particularly, a compound is deemed selective if the ratio is about 2×. More particularly, highly selective compounds can be about 5×, 10×, 20×, 50×, 100×, 200×, 500× or 1000× more active against the sensitive cells than against the non-sensitive cells.

DETAILED DESCRIPTION OF PARTICULAR EMBODIMENTS

Particularly, the invention provides a compound of formula (Ib):

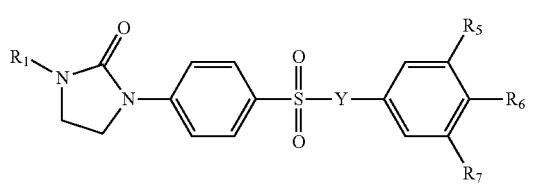

(Ib)

wherein $R_1$ is n-propyl, n-butyl, isobutyl or n-pentyl; Y=O or NH; $R_5$, $R_6$ and $R_7$ is each independently selected from the group consisting of: H, Cl, I, Br, F, or OMe, provided that at least one of $R_5$, $R_6$ and $R_7$ is not H, or a pharmaceutically acceptable derivative or salt thereof.

More particularly, the invention provides a compound of formula (Ib), wherein $R_1$ is n-butyl, isobutyl or n-pentyl; Y=O or NH; $R_5$, $R_6$ and $R_7$ is each independently selected from the group consisting of: H, Cl, I, Br, F, or OMe, provided that at least one of $R_5$, $R_6$ and $R_7$ is not H, or a pharmaceutically acceptable salt thereof.
Particularly, the invention provides a compound of formula (Ib), selected from the group consisting of:
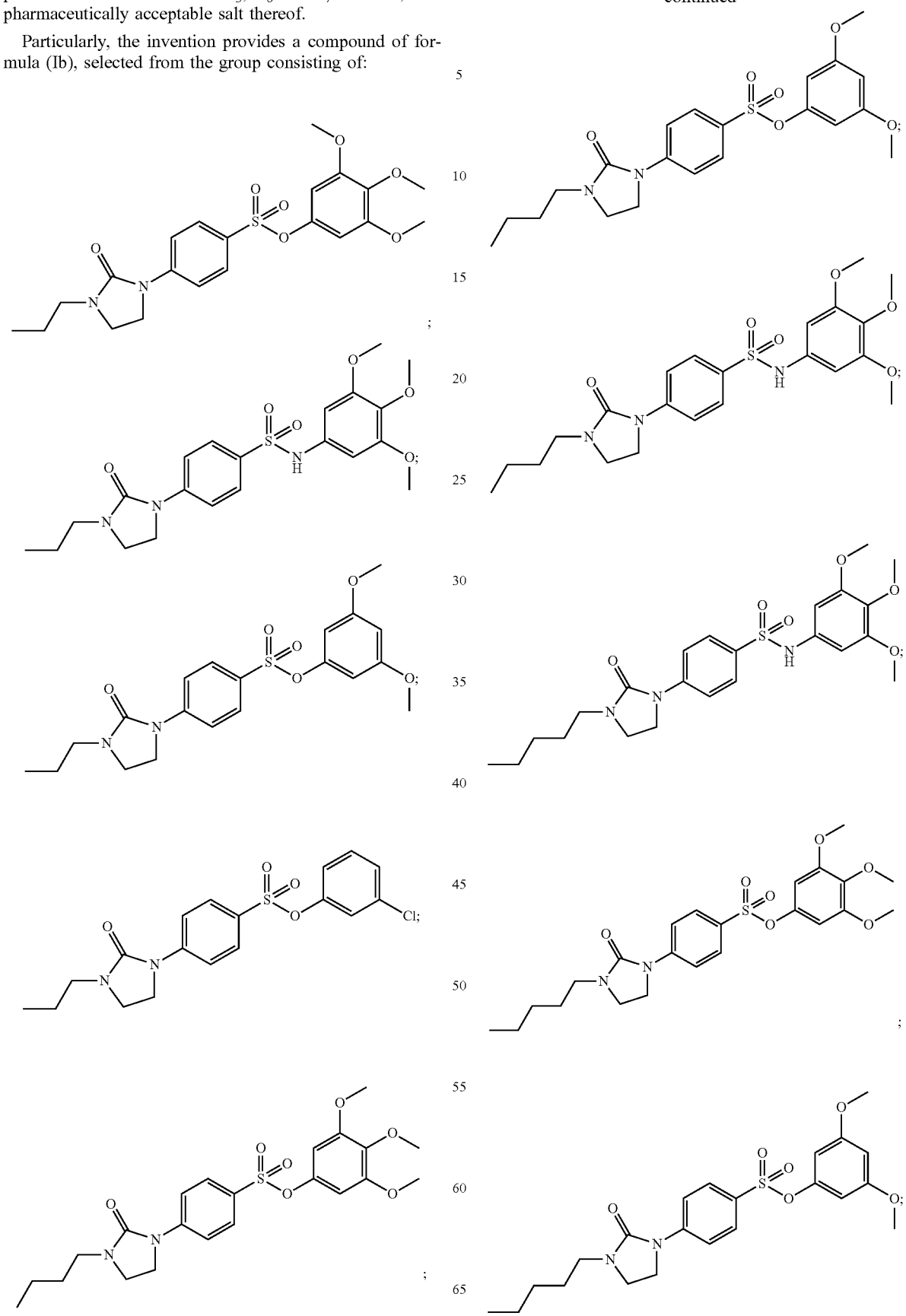

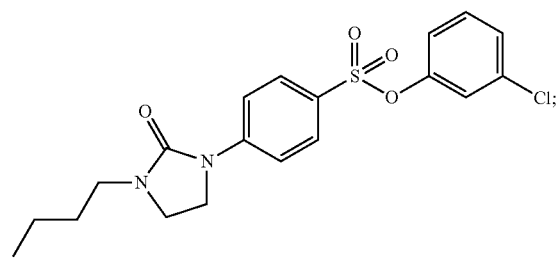
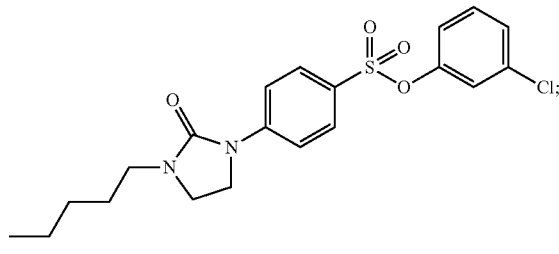
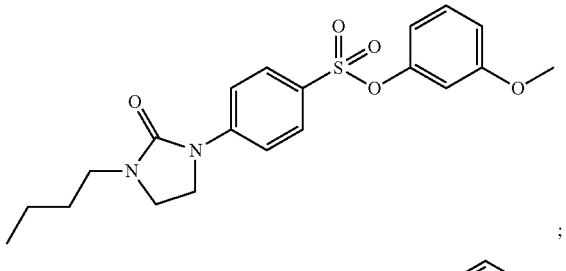
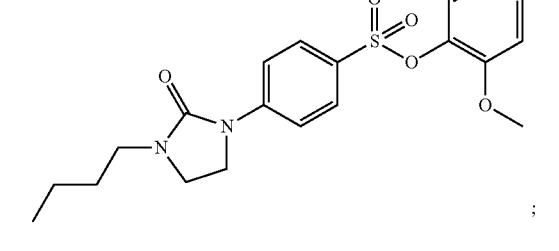
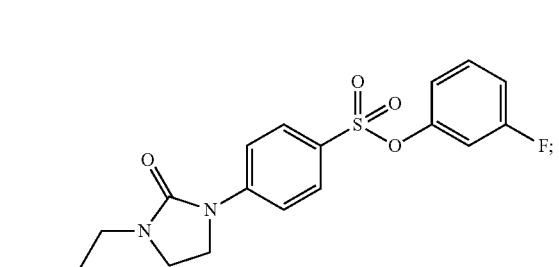
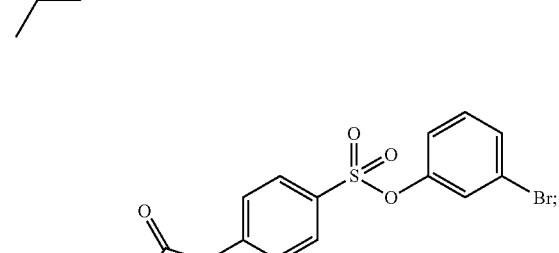
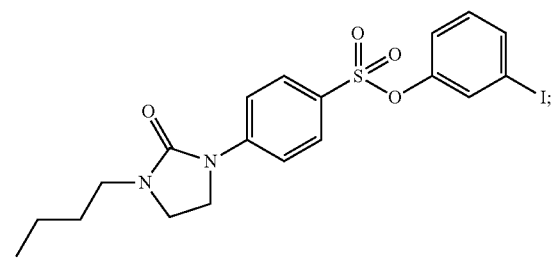
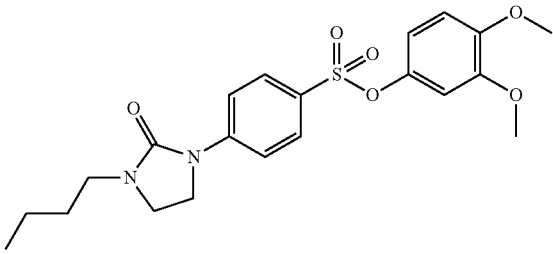
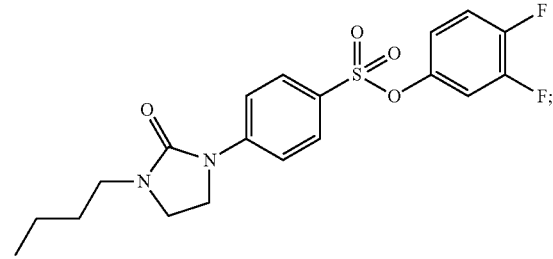
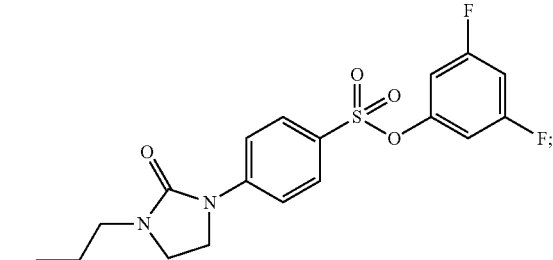
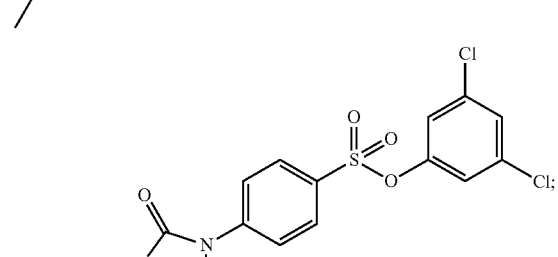
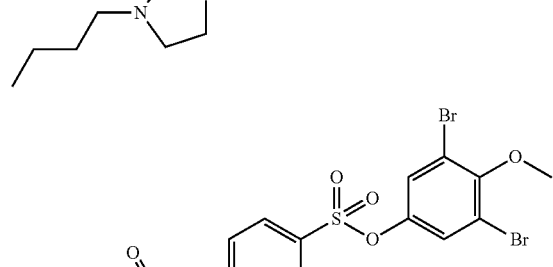

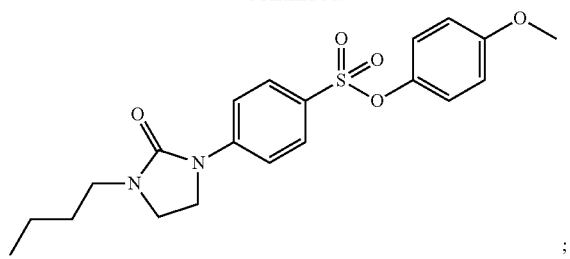;
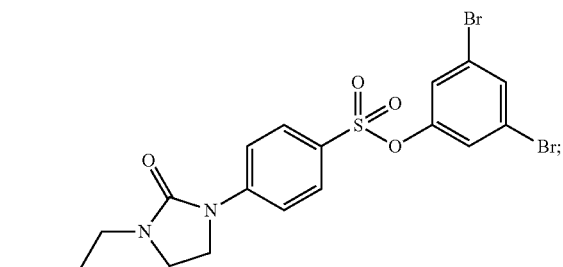;
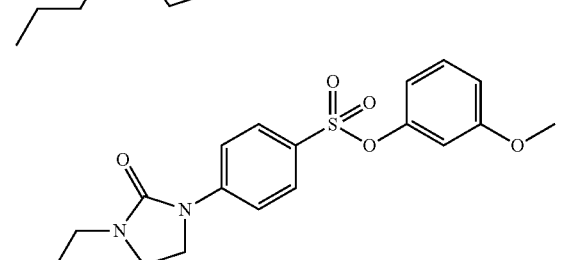;
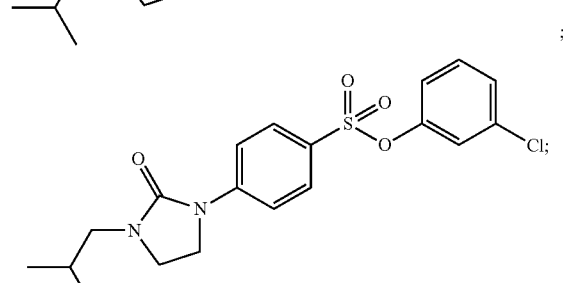;
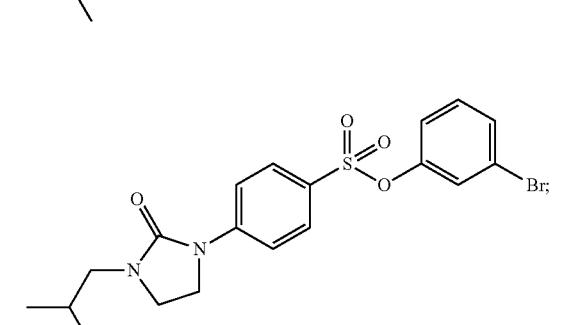;
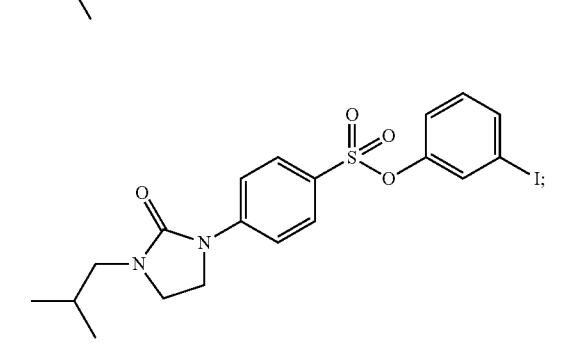;
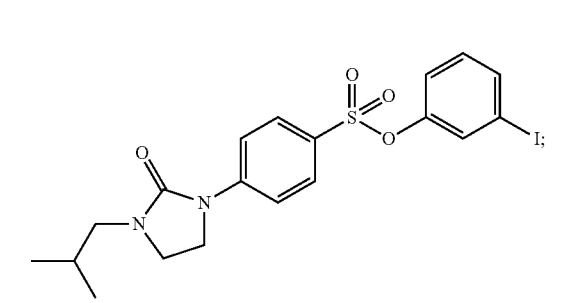;
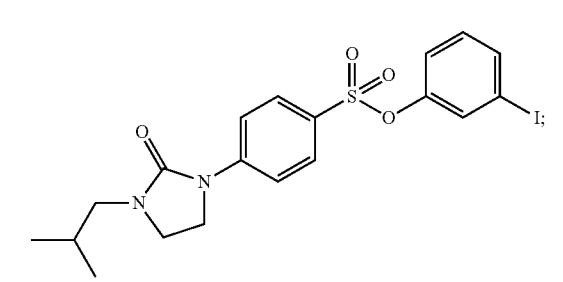;
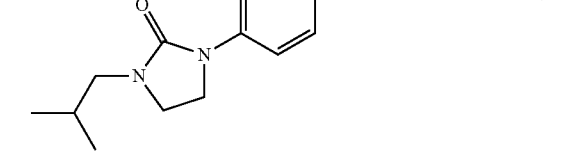;
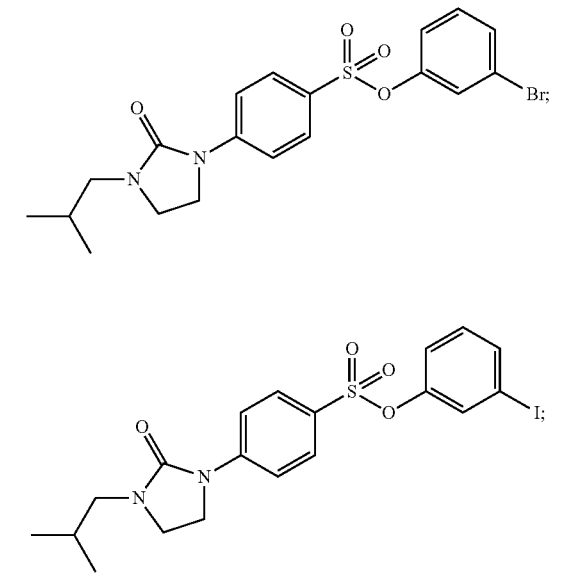;

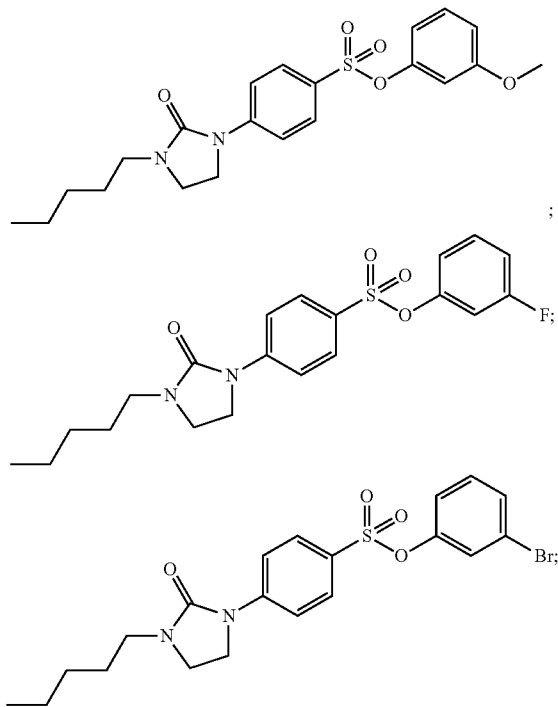
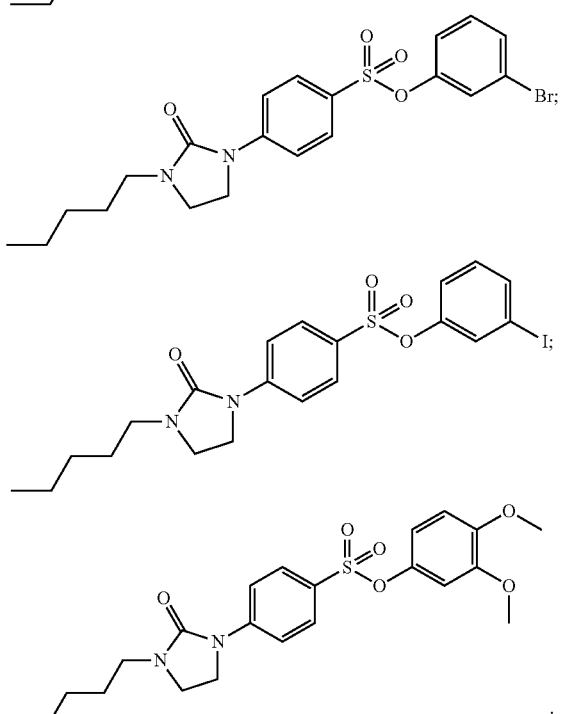
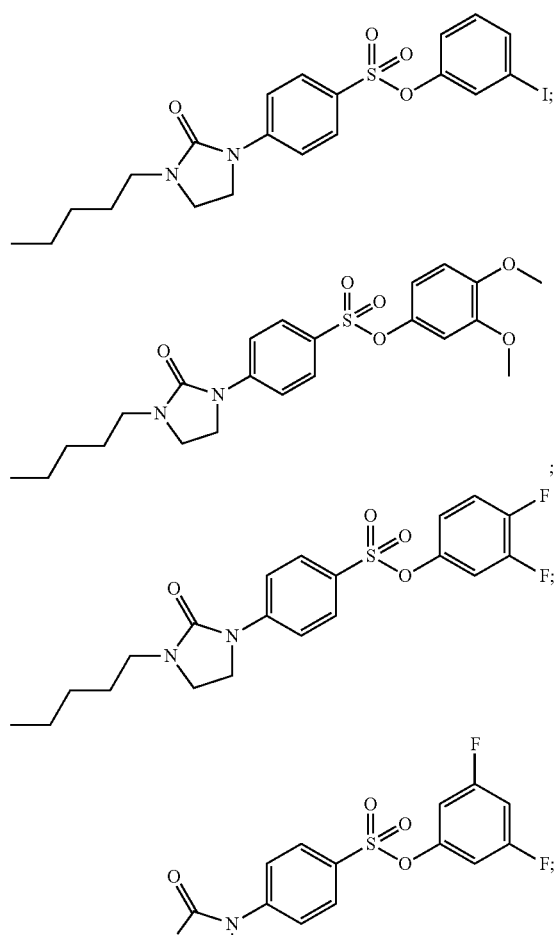
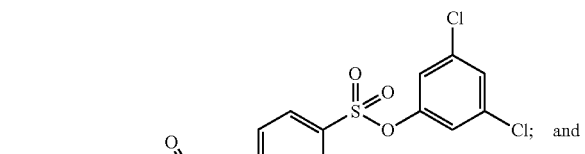
More particularly, the invention provides a compound of formula (Ib), selected from the group consisting of:
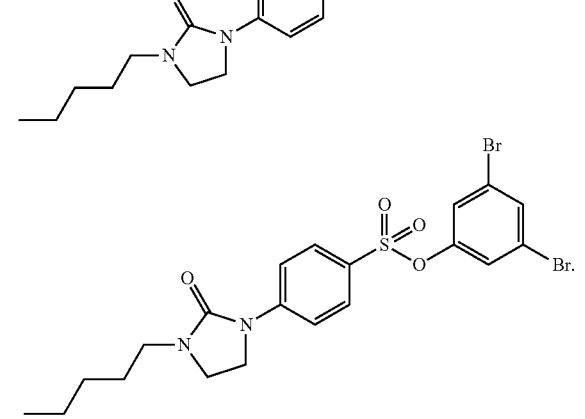
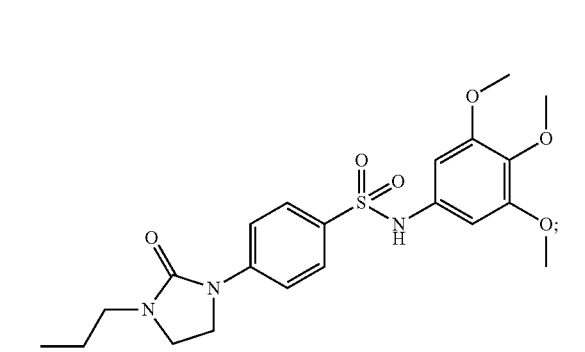
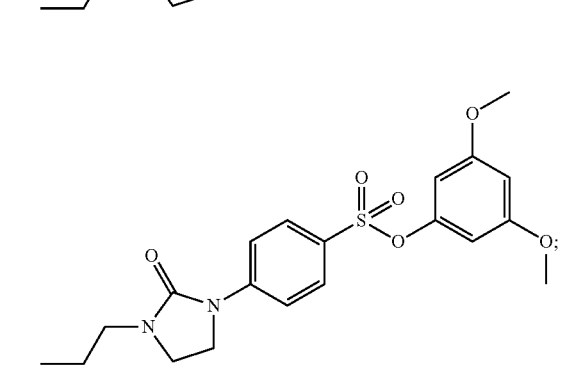

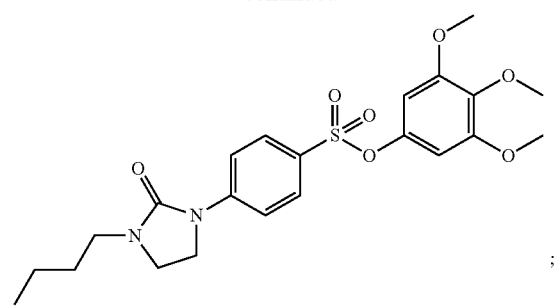
;
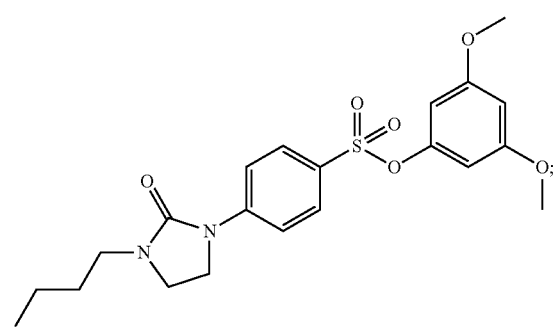
;
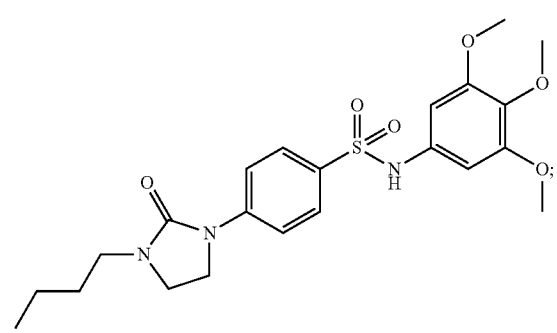
;
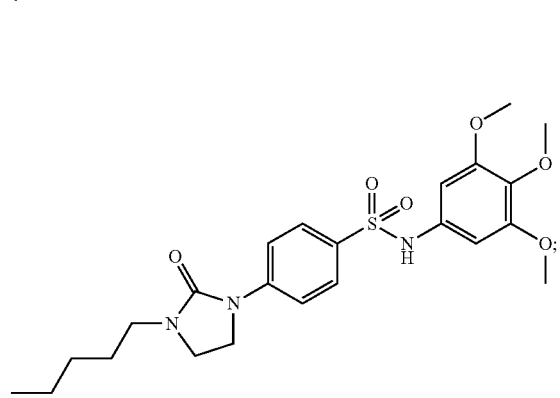
;
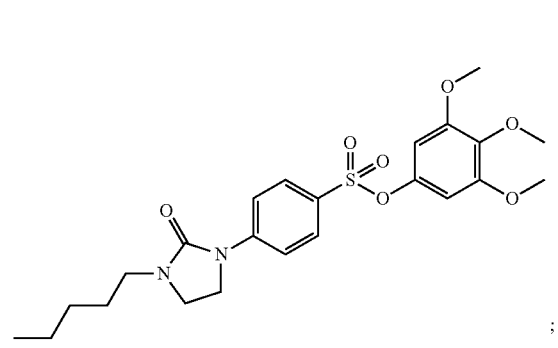
;
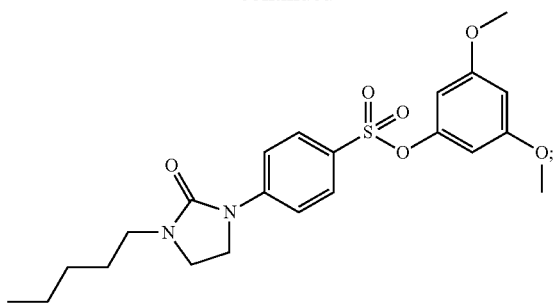
;
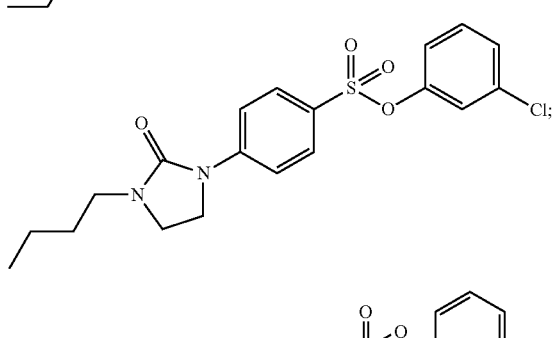
;
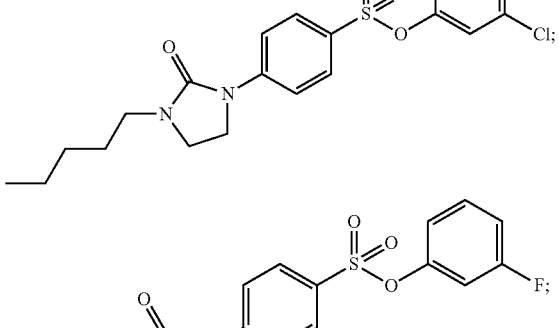
;
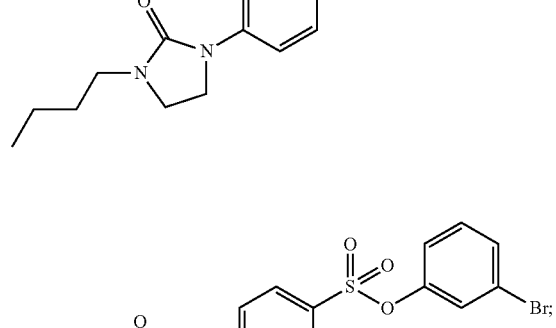
;
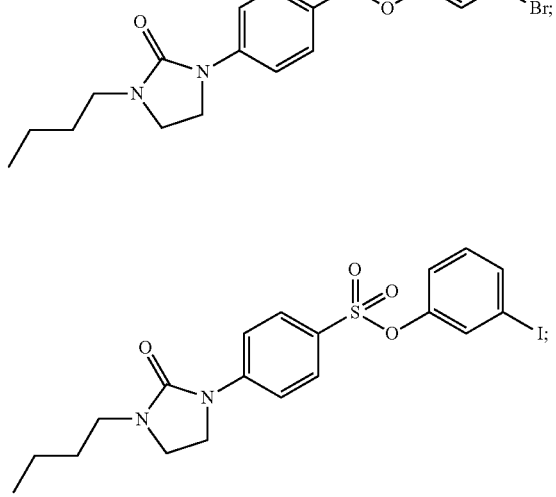
;

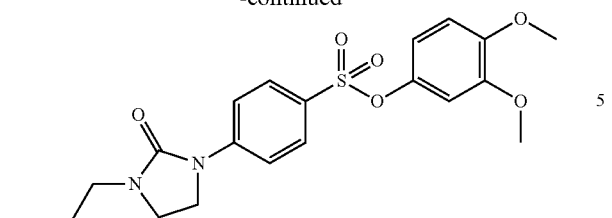
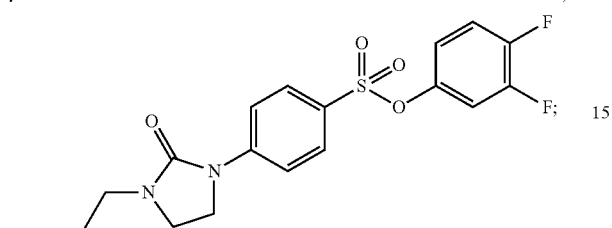
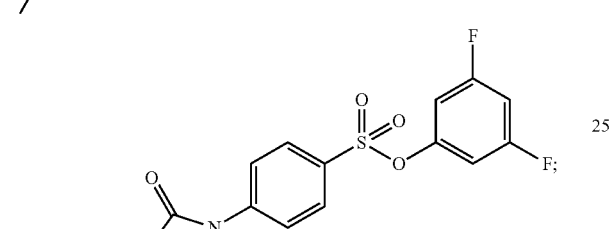
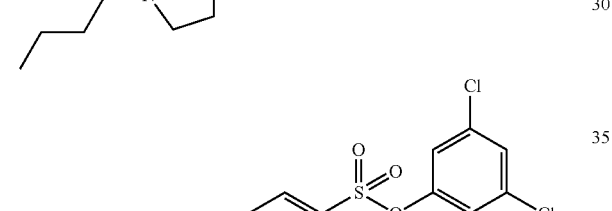
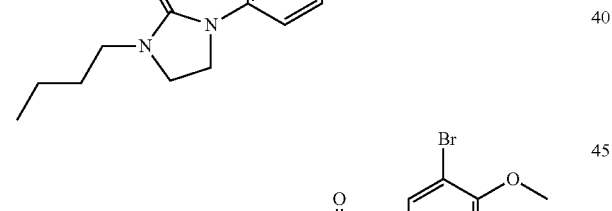
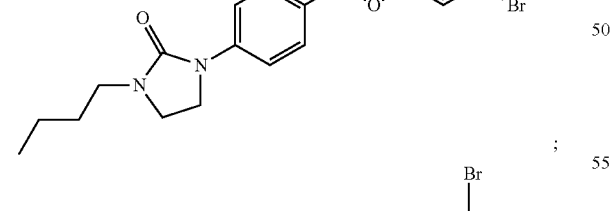
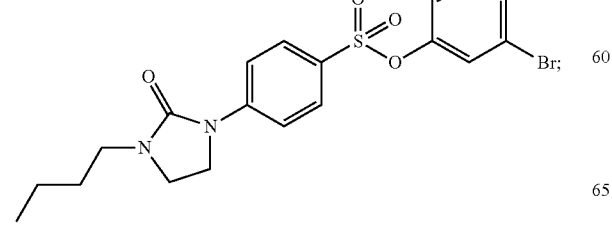
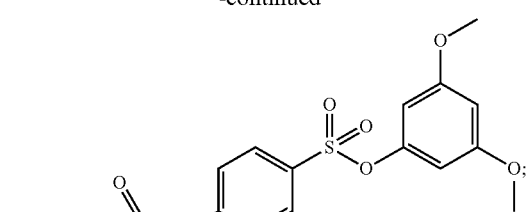
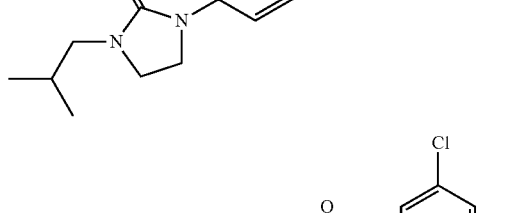
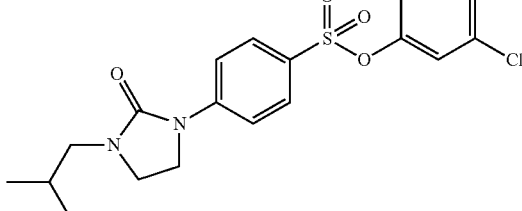
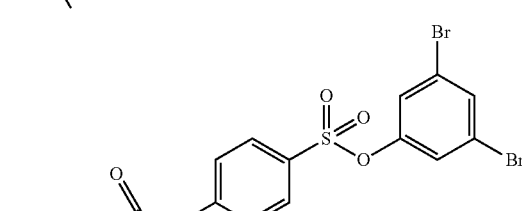
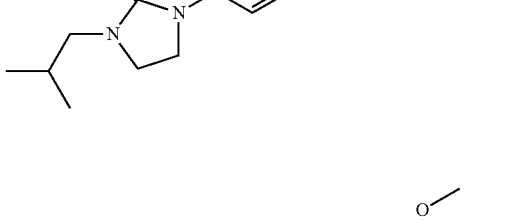
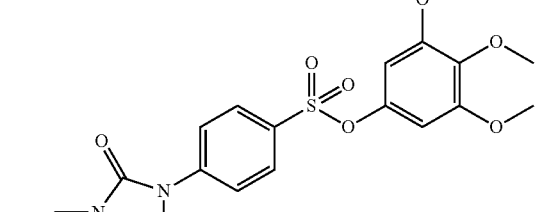
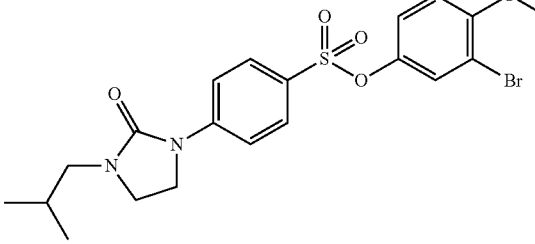

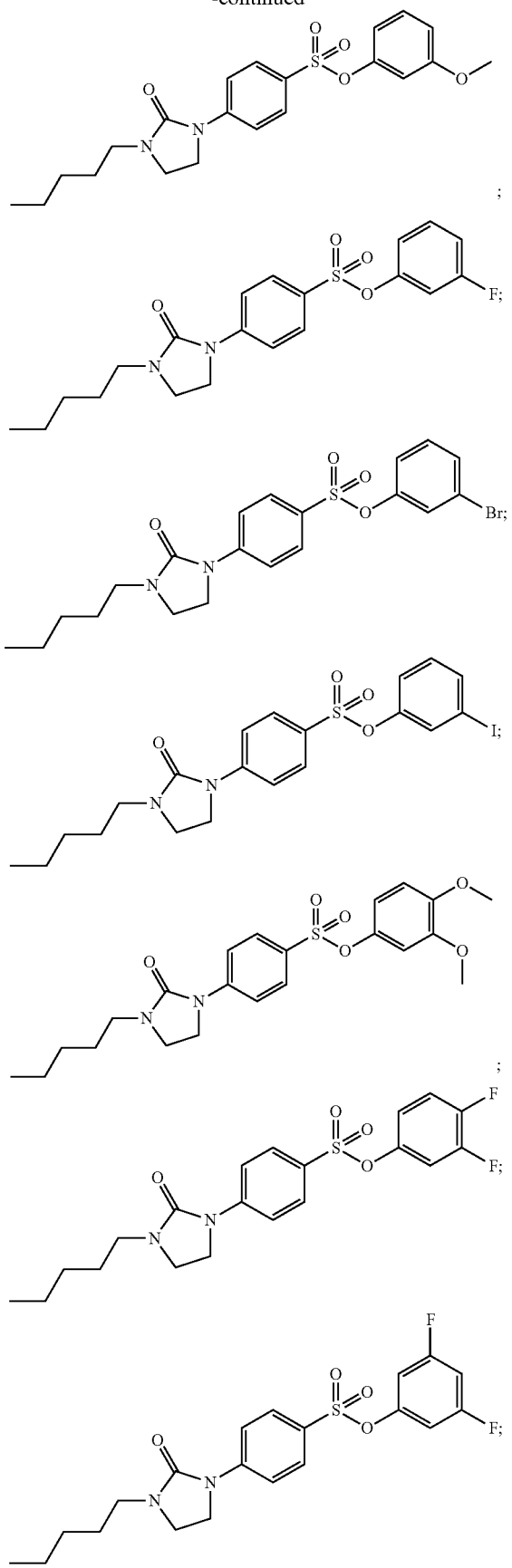

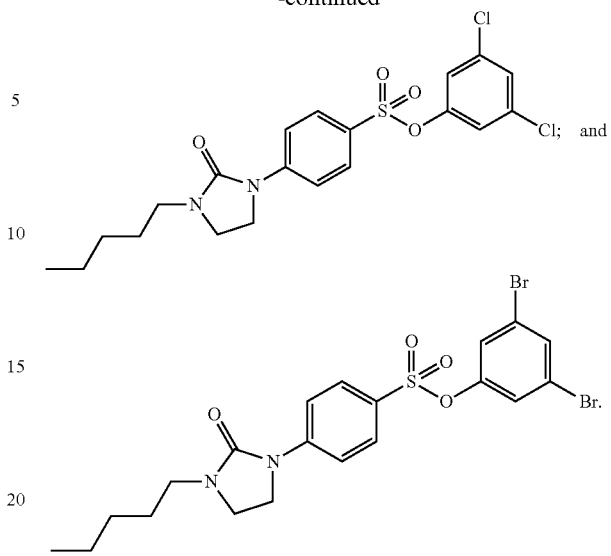

The pharmaceutically-acceptable salts of the compounds of Formulas I to Ib (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, palmoate, pectinate, persulfate, 3-phenylpropionate, picrate, pivalate, propionate, succinate, sulfate, tartrate, thiocyanate, tosylate and undecanoate.

Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; and aralkyl halides like benzyl and phenethyl bromides and others. Preferred acids for forming acid addition salts include HCl, acetic acid, trifluoroacetic acid and fumaric acid.

A further aspect of the present invention is directed to pharmaceutical compositions comprising at least one compound of Formulas (I) to (Ib), or a derivative or salt thereof, and one or more pharmaceutically-acceptable excipients.

A further aspect of the present invention is directed to a method of treating a condition that results from abnormal cell growth, cellular differentiation, tumor growth or invasion with one or more compounds of Formulas (I) to (Ib).

A further aspect of the invention is directed to a method of treating cancer or a metastasis thereof in a human suffering therefrom, particularly wherein the cancer is for example: gastrointestinal, lung, ovarian, prostate, breast, uterine, cervical, comprising administering a therapeutically effective amount of a compound of Formulas (I) to (Ib). More particularly, the cancer is gastrointestinal or breast cancer. Most particularly, the cancer is breast cancer.

A further aspect of the invention is directed to the use of one or more compounds of formulas (I) to (Ib) for the manufacture of medicament for the treatment of cancer or a metastasis thereof in a human. Particularly, the cancer is, for example: gastrointestinal, lung, ovarian, prostate, breast, uterine, cervical cancer. Particularly, the cancer is gastrointestinal or breast cancer. Most particularly, the cancer is breast cancer.

A further aspect of the present invention is directed to a method of synthesizing compounds of Formulas (I) to (Ib) by following the synthetic scheme outlined below.

The compounds of Formulas (I) to (Ib) may also be solvated, especially hydrated. Hydration may occur during manufacturing of the compounds or compositions comprising the compounds, or the hydration may occur over time due to the hygroscopic nature of the compounds.

When any variable occurs more than one time in any constituent of Formulas (I) to (Ib), its definition on each occurrence is independent of its definition at every other occurrence. Also, combinations of substituents and/or variables are permissible only if such combinations result in stable compounds.

The invention disclosed herein is also meant to encompass the in vivo metabolic products of the disclosed compounds. Such products may result, for example, from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabeled compound of the invention, administering it parenterally in a detectable dose to an animal such as rat, mouse, guinea pig, monkey, or to human, allowing sufficient time for metabolism to occur and isolating its conversion products from the urine, blood or other biological samples.

Some of the compounds disclosed herein may contain one or more asymmetric centers and thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

Compositions and Methods of Use

Compositions of the present invention include pharmaceutical compositions comprising a compound of Formulas (I) to (Ib) wherein $R_1$, X, Y, $R_4$, $R_5$, $R_6$, $R_7$ and $R_8$, are defined herein, and one or more pharmaceutically acceptable excipients. Particular compositions of the present invention are pharmaceutical compositions comprising a compound selected from a preferred group of compounds of Formulas (I) to (Ib) as defined above, and one or more pharmaceutically acceptable excipients.

The pharmaceutical compositions of the invention can be administered to any animal that can experience the beneficial effects of the compounds of the invention. Foremost among such animals are mammals, particularly humans, although the invention is not intended to be so limited.

The pharmaceutical compositions of the present invention can be administered by any means that achieve their intended purpose. For example, administration can be by subcutaneous, intravenous, intramuscular, intraperitoneal, buccal, or ocular routes, rectally, parenterally, intrasystemically, intravaginally, topically (as by powders, ointments, drops or transdermal patch), or as an oral or nasal spray. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropyl methylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which can contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate, triglycerides, Tween® 80, propylene glycol, tetraglycol, cremophor EL or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredients in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquefied gas propellant. The liquefied propellant medium and indeed the total composition are preferably such that the active ingredients do not dissolve therein to any substantial extent. The pressurized composition may also contain a surface-active agent. The surface-active agent may be a liquid or solid non-ionic surface-active agent or may be a solid anionic surface-active agent. It is preferred to use the solid anionic surface-active agent in the form of a sodium salt.

Compositions for rectal or vaginal administration are preferably suppositories which can be prepared by mixing the compounds of the present invention with suitable non-irritating excipients or carriers such as cocoa butter, polyethylene glycol or a suppository wax which are solid at room temperature but liquid at body temperature and therefore melt in the rectum or vaginal cavity and release the drugs.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., Meth. Cell Biol. 14:33 (1976)).

Compounds of the present invention are useful for treating, inhibiting or preventing abnormal cell growth, cellular differentiation, tumor growth and invasion. They are effective against a broad range of cancers that may include gastrointestinal, lung, ovarian, prostate, breast, uterine, cervical, and metastasis thereof to another organ. These cancers and conditions are merely meant to be illustrative and are by no means meant to be a limiting or exhaustive list.

The compounds of the present invention may be administered in an effective amount within the dosage range of about 0.0005 mg/kg to about 200 mg/kg, preferably from about 0.001 mg/kg to about 100 mg/kg body weight. The compounds are preferably administered in compositions in which the compound is present in a concentration of about 1 mg/mL to about 250 mg/mL (e.g., in a solution), or in an amount of about 1 mg to about 200 mg, preferably about 5 mg to about 100 mg (e.g., in one unit of a solid dosage form such as a tablet or capsule). When the composition is in the form of a tablet, the compound of the present invention may comprise about 1 to about 50% (wt/wt), preferably about 5 to about 25% (wt/wt) of the tablet. Compounds of the present invention may be administered in a single daily dose, or the total daily dosage may be administered in divided doses of two, three or four times daily.

The compounds and compositions according to the invention may also be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Preparation of Compounds of Formula (I)

Scheme 1:

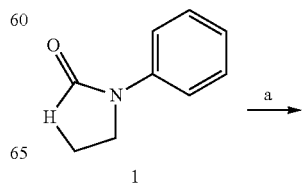

1

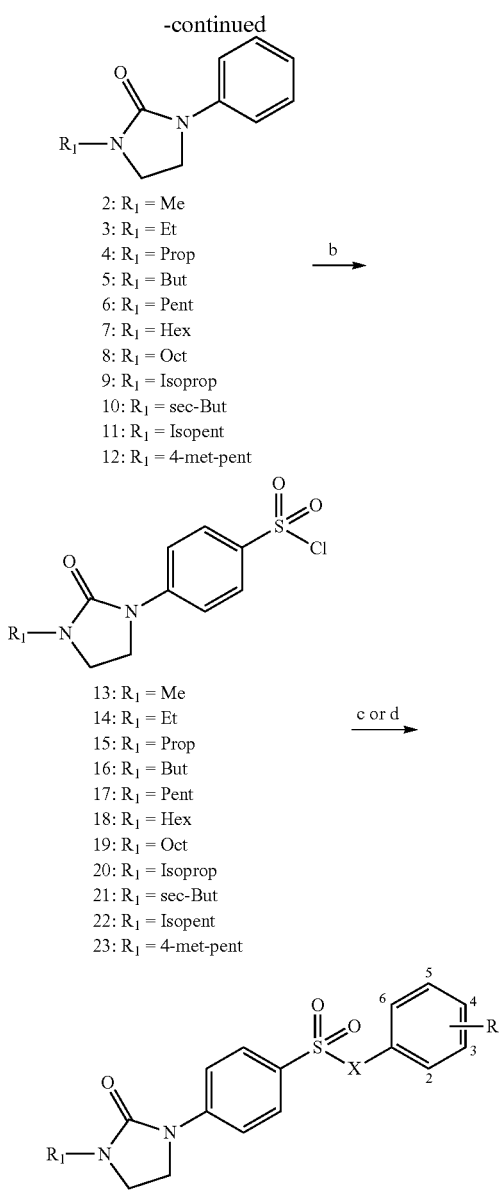

Scheme 1: Reagents: (a) NaH (60%), MeI (methyl iodide), EtI (ethyl iodide), PrI (propyl iodide), ButI (butyl iodide), PentI (pentyl iodide), HexI (hexyl iodide), OctI (octyl iodide), IsopropI (isopropyl iodide), sec-ButI (sec-butyl iodide), IsopentI or 4-met-pent) (isopentyl iodide)/THF; (b) ClSO$_3$H/CCl$_4$; (c) relevant phenol, TEA/DCM; (d) relevant aniline, DMAP/CH$_3$CN.

General Preparation of Compounds 1

Syntheses and characterization of compound 1 were previously reported (Fortin, S.; Wei, L.; Moreau, E.; Lacroix, J.; Cote, M.-F.; Petitclerc, E.; P. Kotra, L.; C.-Gaudreault, R. *J. Med. Chem.* 2011, 54, 4559-4580). 2-Chloroethylisocyanate (1.2 eq.) was added dropwise to a cold solution (ice bath) of the required aniline (1.0 eq.) in dry methylene chloride (15 mL per g of aniline). The ice bath was then removed and the reaction mixture was stirred at room temperature for 24 h. After completion of the reaction, the solvent was evaporated under reduced pressure to give white solid, which was triturated twice in a mixture of cold hexanes/ether 10:1. Afterwards, sodium hydride (3 eq.) was added slowly to a cold solution of the white solid (1 eq.) in tetrahydrofuran under dry nitrogen atmosphere. The ice bath was then removed after 30 min and the reaction mixture was stirred at room temperature for 5 h. The reaction was quenched at 0° C. with water and diluted with ethyl acetate. The organic layer was washed with water, brine and dried over anhydrous sodium sulfate, filtered, and concentrated in vacuo to provide compound 1, which was used without further purification. Compound 1 was also prepared using a method described by Neville. Briefly, triphosgene (12.2 mmol) was dissolved in 40 mL of dry tetrahydrofuran and cooled at 0° C. N-phenylethylenediamine (36.7 mmol) dissolved in 65 mL of tetrahydrofuran and 7.7 mL of triethylamine was added over a period of 30 min to the triphosgene solution. A white solid immediately precipitated and the reaction was complete after 5 min. The reaction mixture was quenched with water and diluted with ethyl acetate. The organic layer was washed with water, brine and dried over anhydrous sodium sulfate, filtered, and concentrated in vacuo. The residue was purified by flash chromatography (methylene chloride to methylene chloride/ethyl acetate 3:10) to afford a white solid.

General Preparation of Compounds 2 to 12

Sodium hydride 60% (33 mmol) was added slowly to a cold solution of 1 (30 mmol) in dry tetrahydrofuran under a dry nitrogen atmosphere. The ice bath was then removed after 30 min and the required alkyliodide (36 mmol) was then added slowly. The reaction mixture was stirred at room temperature for 20 h. The reaction was quenched at 0° C. with water and diluted with ethyl acetate. The organic layer was washed with water, brine and dried over anhydrous sodium sulfate, filtered, and concentrated in vacuo. The residue was purified by flash chromatography (silica gel, methylene chloride to methylene chloride/ethyl acetate (85:15)).

General Preparation of Compounds 13 to 23

To 1.5 mL (23.1 mmol) of chlorosulfonic acid in 3 mL of carbon tetrachloride at 0° C. was added slowly (3.1 mmol) the required compound 2 to 12. The reaction was almost completed after 4 h at 0° C. The reaction mixture was then slowly poured onto ice water, filtered to collect a solid. The mixture solution was extracted thrice with methylene chloride. Afterward, the combined methylene chloride fractions were washed with brine, dried over anhydrous MgSO$^4$, filtered, evaporated under reduced pressure and the two solids were combined and dried under vacuum.

General preparation of phenyl alkyl-2-oxoimidazolidin-1-yl)benzenesulfonates (Method A) and phenyl alkyl-2-oxoimidazolidin-1-yl)benzenesulfonamides (Method B)

Method A (Sulfonates): 4-(2-oxo-3-alkylimidazolidin-1-yl)benzene-1-sulfonyl chloride (8.00 mmol) was suspended in dry methylene chloride (10 mL) under a dry nitrogen atmosphere. The required phenol (8.00 mmol) and triethylamine (8.00 mmol) were successively added dropwise to the suspension and the mixture was stirred at room temperature for 24 h. Then, hydrochloric acid 1N was added to the mixture and extracted twice with methylene chloride. The combined methylene chloride fractions were washed with sodium hydroxide 1N, brine, dried over sodium sulfate, filtered, and evaporated under vacuum. The white solid was purified by flash chromatography on silica gel using the appropriate eluent mixture.

Method B (Sulfonamides): 4-(2-oxo-3-alkylimidazolidin-1-yl)benzene-1-sulfonyl chloride (1.00 mmol) was suspended in dry acetonitrile (10 mL) under dry nitrogen atmosphere. The required aniline (1.00 mmol) and 4-dimethylaminopyridine (4.00 mmol) were successively added dropwise to the suspension and the mixture was stirred at room temperature for 48 h. Ethyl acetate was added and the solution was washed with hydrochloric acid 1N, brine, dried over anhydrous sodium sulfate, filtered, and evaporated to dryness under vacuum. The white solid was purified by flash chromatography on silica gel using the appropriate eluent mixture.

EXAMPLES OF SPECIFIC COMPOUNDS

Example 1

Intermediate Compounds 2-12

1-phenyl-3-propylimidazolidin-2-one (4). Yield: 56%; Yellow solid; mp: 59-60° C.; IR: 2925, 1684 cm$^{-1}$; $^1$H NMR (CDCl$_3$) δ 7.56-7.53 (m, 2H, Ar), 7.33-7.27 (m, 2H, Ar), 7.02-6.97 (m, 1H, Ar), 3.77-3.72 (m, 2H, CH$_2$), 3.44-3.39 (m, 2H, CH$_2$), 3.23 (t, 2H, J=7.4 Hz, CH$_2$), 1.63-1.51 (m, 2H, CH$_2$), 0.93 (t, 3H, J=7.4 Hz, CH$_3$); $^{13}$C NMR (CDCl$_3$) δ 157.9, 140.8, 128.7, 122.1, 117.2, 45.7, 42.4, 41.7, 20.8, 11.3.

Example 2

Intermediate Compounds 13 to 23

4-(2-oxo-3-propylimidazolidin-1-yl)benzene-1-sulfonyl chloride (15). Yield: 88%; White solid; mp: 141-143° C.; IR: 2961, 1700 cm$^{-1}$; $^1$H NMR (CDCl$_3$) δ 7.98-7.95 (m, 2H, Ar), 7.81-7.78 (m, 2H, Ar), 3.92-3.87 (m, 2H, CH$_2$), 3.60-3.55 (m, 2H, CH$_2$), 3.30 (t, 2H, J=7.3 Hz, CH$_2$), 1.68-1.56 (m, 2H, CH$_2$), 0.96 (t, 3H, J=7.4 Hz, CH$_3$); $^{13}$C NMR (CDCl$_3$) δ 156.6, 146.7, 136.3, 128.5, 116.4, 45.6, 42.2, 41.3, 20.6, 11.2.

Example 3

Sulfonates (Method A)

o-Tolyl 4-(2-oxo-3-propylimidazolidin-1-yl)benzenesulfonate. Flash chromatography (methylene chloride to methylene chloride/ethyl acetate (95:5)). Yield: 86%; White solid; mp: 139-141° C.; IR: 2968, 1698 cm$^{-1}$; $^1$H NMR (CDCl$_3$) δ 7.73-7.66 (m, 4H, Ar), 7.11-7.04 (m, 3H, Ar), 6.96-6.93 (m, 1H, Ar), 3.83-3.78 (m, 2H, CH$_2$), 3.53-3.48 (m, 2H, CH$_2$), 3.27-3.22 (m, 2H, CH$_2$), 2.05 (s, 3H, CH$_3$), 1.63-1.51 (m, 2H, CH$_2$), 0.92 (t, 3H, J=7.4 Hz, CH$_3$); $^{13}$C NMR (CDCl$_3$) δ 156.9, 148.4, 145.9, 131.6, 129.5, 127.6, 126.9, 126.9, 122.3, 116.1, 45.6, 42.1, 41.3, 20.6, 16.3, 11.2; HRMS (ES+) m/z found 375.1235; C$_{19}$H$_{23}$N$_2$O$_4$S (M$^+$+H) requires 375.1379.

2-Ethylphenyl 4-(2-oxo-3-propylimidazolidin-1-yl)benzenesulfonate. Flash chromatography (methylene chloride to methylene chloride/ethyl acetate (95:5)). Yield: 86%; White solid; mp: 103-105° C.; IR: 2970, 1697 cm$^{-1}$; $^1$H NMR (CDCl$_3$) δ 7.74-7.66 (m, 4H, Ar), 7.18-7.04 (m, 3H, Ar), 6.97-6.94 (m, 1H, Ar), 3.82-3.76 (m, 2H, CH$_2$), 3.52-3.47 (m, 2H, CH$_2$), 3.26-3.21 (m, 2H, CH$_2$), 2.48 (q, 2H, J=7.5 Hz, CH$_2$), 1.60-1.53 (m, 2H, CH$_2$), 1.08 (t, 3H, J=7.5 Hz, CH$_3$), 0.92 (t, 3H, J=7.3 Hz, CH$_3$); $^{13}$C NMR (CDCl$_3$) δ 156.9, 147.9, 145.9, 137.3, 129.8, 129.4, 127.6, 127.1, 126.8, 122.0, 116.2, 45.6, 42.1, 41.3, 22.8, 20.6, 14.1, 11.2; HRMS (ES+) m/z found 389.1161; C$_{20}$H$_{25}$N$_2$O$_4$S (M$^+$+H) requires 389.1535.

2-propylphenyl 4-(2-oxo-3-propylimidazolidin-1-yl)benzenesulfonate. Flash chromatography (methylene chloride to methylene chloride/ethyl acetate (95:5)). Yield: 92%; White solid; mp: 85-87° C.; IR: 2960, 1699 cm$^{-1}$; $^1$H NMR (CDCl$_3$) δ 7.75-7.66 (m, 4H, Ar), 7.14-7.05 (m, 3H, Ar), 6.98-6.96 (m, 1H, Ar), 3.81-3.76 (m, 2H, CH$_2$), 3.51-3.46 (m, 2H, CH$_2$), 3.26-3.21 (m, 2H, CH$_2$), 2.43-2.38 (m, 2H, CH$_2$), 1.65-1.43 (m, 4H, 2x CH$_2$), 0.91 (t, 3H, J=7.3 Hz, CH$_3$), 0.84 (t, 3H, J=7.4 Hz, CH$_3$); $^{13}$C NMR (CDCl$_3$) δ 156.9, 148.1, 145.9, 135.8, 130.6, 129.4, 127.7, 126.9, 126.9, 122.0, 116.2, 45.6, 42.1, 41.3, 31.8, 23.0, 20.6, 13.9, 11.2; HRMS (ES+) m/z found 403.1477; C$_{21}$H$_{27}$N$_2$O$_4$S (M$^+$+H) requires 403.1692.

2-Methoxyphenyl 4-(2-oxo-3-propylimidazolidin-1-yl)benzenesulfonate. Flash chromatography (methylene chloride to methylene chloride/ethyl acetate (95:5)). Yield: 81%; White solid; mp: 136-138° C.; IR: 2965, 1697 cm$^{-1}$; $^1$H NMR (CDCl$_3$) δ 7.75-7.64 (m, 4H, Ar), 7.18-7.08 (m, 2H, Ar), 6.87-6.79 (m, 2H, Ar), 3.84-3.79 (t, 2H, J=8.7 Hz, CH$_2$), 3.55-3.49 (m, 5H, CH$_2$ and CH$_3$), 3.27-3.23 (m, 2H, CH$_2$), 1.64-1.52 (m, 2H, CH$_2$), 0.93 (t, 3H, J=7.4 Hz, CH$_3$); $^{13}$C NMR (CDCl$_3$) δ 156.9, 151.9, 145.7, 138.5, 129.7, 128.0, 127.8, 124.0, 120.6, 115.9, 112.8, 55.7, 45.6, 42.1, 41.3, 20.6, 11.3; HRMS (ES+) m/z found 391.0341; C$_{19}$H$_{23}$N$_2$O$_5$S (M$^+$+H) requires 391.1328.

2,4-Dimethylphenyl 4-(2-oxo-3-propylimidazolidin-1-yl) benzenesulfonate. Flash chromatography (methylene chloride to methylene chloride/ethyl acetate (95:5)). Yield: 86%; White solid; mp: 85-87° C.; IR: 2930, 1699 cm$^{-1}$, $^1$H NMR (CDCl$_3$) δ 7.75-7.67 (m, 4H, Ar), 6.92-6.80 (m, 3H, Ar), 3.85-3.80 (m, 2H, CH$_2$), 3.55-3.49 (m, 2H, CH$_2$), 3.29-3.24 (m, 2H, CH$_2$), 2.25 (s, 3H, CH$_3$), 2.02 (s, 3H, CH$_3$), 1.65-1.53 (m, 2H, CH$_2$), 0.94 (t, 3H, J=7.4 Hz, CH$_3$); $^{13}$C NMR (CDCl$_3$) δ 156.9, 146.2, 145.8, 136.7, 132.2, 131.1, 129.5, 127.8, 127.4, 122.0, 116.1, 45.6, 42.1, 41.3, 20.8, 20.6, 16.3, 11.3; HRMS (ES+) m/z found 389.1159; C$_{20}$H$_{25}$N$_2$O$_4$S (M$^+$+H) requires 389.1535.

2,4,5-Trichlorophenyl 4-(2-oxo-3-propylimidazolidin-1-yl)benzenesulfonate. Flash chromatography (methylene chloride to methylene chloride/ethyl acetate (95:5)). Yield: 87%; White solid; mp: 125-127° C.; IR: 2932, 1699 cm$^{-1}$; $^1$H NMR (CDCl$_3$) δ 7.79-7.70 (m, 4H, Ar), 7.45 (s, 1H, Ar), 7.41 (s, 1H, Ar), 3.87-3.81 (m, 2H, CH$_2$), 3.56-3.51 (m, 2H, CH$_2$), 3.29-3.24 (m, 2H, CH$_2$), 1.65-1.52 (m, 2H, CH$_2$), 0.93 (t, 3H, J=7.4 Hz, CH$_3$); $^{13}$C NMR (CDCl$_3$) δ 156.7, 146.5, 144.3, 131.6, 131.5, 131.3, 129.9, 126.8, 126.2, 125.7, 116.2, 45.6, 42.1, 41.3, 20.6, 11.2; HRMS (ES+) m/z found 462.8655; C$_{18}$H$_{18}$Cl$_3$N$_2$O$_4$S (M$^+$+H) requires 463.0053.

2,4,6-Trichlorophenyl 4-(2-oxo-3-propylimidazolidin-1-yl)benzenesulfonate. Flash chromatography (methylene chloride to methylene chloride/ethyl acetate (95:5)). Yield: 73%; White solid; mp: 109-111° C.; IR: 2929, 1700 cm$^{-1}$; $^1$H NMR (CDCl$_3$) δ 7.88-7.85 (m, 2H, Ar), 7.75-7.72 (m, 2H, Ar), 7.30 (s, 2H, Ar), 3.87-3.82 (m, 2H, CH$_2$), 3.55-3.50 (m, 2H, CH$_2$), 3.28-3.23 (m, 2H, CH$_2$), 1.64-1.52 (m, 2H, CH$_2$), 0.93 (t, 3H, J=7.4 Hz, CH$_3$); $^{13}$C NMR (CDCl$_3$) δ 156.8, 146.4, 142.4, 132.7, 130.9, 129.8, 129.1, 128.2, 116.1, 45.6, 42.1, 41.3, 20.6, 11.3; HRMS (ES+) m/z found 462.8724; C$_{18}$H$_{18}$Cl$_3$N$_2$O$_4$S (M$^+$+H) requires 463.0053.

m-Tolyl 4-(2-oxo-3-propylimidazolidin-1-yl)benzenesulfonate. Flash chromatography (methylene chloride to methylene chloride/ethyl acetate (95:5)). Yield: 77%; White solid; mp: 76-78° C.; IR: 2932, 1700 cm$^{-1}$; $^1$H NMR (CDCl$_3$) δ 7.71-7.68 (m, 4H, Ar), 7.12-6.98 (m, 2H, Ar), 6.83 (s, 1H, Ar), 6.68-6.66 (m, 1H, Ar), 3.83-3.77 (m, 2H, CH$_2$), 3.53-3.48 (m, 2H, CH$_2$), 3.27-3.22 (m, 2H, CH$_2$), 2.25 (s, 3H, CH$_3$), 1.63-1.51 (m, 2H, CH$_2$), 0.92 (t, 3H, J=7.4 Hz, CH$_3$); $^{13}$C NMR (CDCl$_3$) δ 156.9, 149.6, 145.8, 140.0, 129.6, 129.2, 127.8, 127.0, 123.0, 119.1, 116.1, 45.6, 42.1, 41.3, 21.2, 20.6, 11.2; HRMS (ES+) m/z found 375.1241; $C_{19}H_{23}N_2O_4S$ (M$^+$+H) requires 375.1379.

3-Methoxyphenyl 4-(2-oxo-3-propylimidazolidin-1-yl)benzenesulfonate. Flash chromatography (methylene chloride to methylene chloride/ethyl acetate (95:5)). Yield: 79%; White solid; mp: 64-66° C.; IR: 2966, 1695 cm$^{-1}$; $^1$H NMR (CDCl$_3$) δ 7.70-7.67 (m, 4H, Ar), 7.12-7.07 (m, 1H, Ar), 6.74-6.70 (m, 1H, Ar), 6.53-6.47 (m, 2H, Ar), 3.81-3.75 (m, 2H, CH$_2$), 3.67 (s, 3H, CH$_3$), 3.50-3.46 (m, 2H, CH$_2$), 3.25-3.20 (m, 2H, CH$_2$), 1.62-1.50 (m, 2H, CH$_2$), 0.91 (t, 3H, J=7.4 Hz, CH$_3$); $^{13}$C NMR (CDCl$_3$) δ 160.4, 156.8, 150.5, 145.9, 129.9, 129.6, 126.8, 116.1, 114.3, 112.9, 108.4, 55.5, 45.5, 42.1, 41.3, 20.6, 11.2; HRMS (ES+) m/z found 391.1241; $C_{19}H_{23}N_2O_5S$ (M$^+$+H) requires 391.1328.

3-Fluorophenyl 4-(2-oxo-3-propylimidazolidin-1-yl)benzenesulfonate.
Flash chromatography (methylene chloride to methylene chloride/ethyl acetate (95:5)). Yield: 74%; White solid; mp: 89-91° C.; IR: 2666, 1701 cm$^{-1}$; $^1$H NMR (CDCl$_3$) δ 7.73-7.64 (m, 4H, Ar), 7.23-7.15 (m, 1H, Ar), 6.93-6.88 (m, 1H, Ar), 6.73-6.70 (m, 2H, Ar), 3.82-3.80 (m, 2H, CH$_2$), 3.53-3.47 (m, 2H, CH$_2$), 3.25-3.21 (m, 2H, CH$_2$), 1.62-1.49 (m, 2H, CH$_2$), 0.90 (t, 3H, J=7.4 Hz, CH$_3$); $^{13}$C NMR (CDCl$_3$) δ 164.2, 160.9, 156.8, 150.3, 150.2, 146.2, 130.5, 130.3, 129.6, 126.2, 118.2, 118.2, 116.2, 114.4, 114.1, 110.7, 110.3, 45.5, 42.1, 41.2, 20.6, 11.2; HRMS (ES+) m/z found 379.1007; $C_{18}H_{20}FN_2O_4S$ (M$^+$+H) requires 379.1128.

3-Nitrophenyl 4-(2-oxo-3-propylimidazolidin-1-yl)benzenesulfonate. Flash chromatography (methylene chloride to methylene chloride/ethyl acetate (95:5)). Yield: 79%; White solid; mp: 116-118° C.; IR: 2958, 1711 cm$^{-1}$; $^1$H NMR (CDCl$_3$) δ 8.09-8.06 (m, 1H, Ar), 7.82-7.81 (m, 1H, Ar), 7.73-7.67 (m, 4H, Ar), 7.49-7.43 (m, 1H, Ar), 7.33-7.30 (m, 1H, Ar), 3.86-3.80 (m, 2H, CH$_2$), 3.56-3.50 (m, 2H, CH$_2$), 3.27-3.22 (m, 2H, CH$_2$), 1.63-1.51 (m, 2H, CH$_2$), 0.91 (t, 3H, J=7.4 Hz, CH$_3$); $^{13}$C NMR (CDCl$_3$) δ 156.7, 149.8, 148.7, 146.5, 130.4, 129.7, 128.8, 125.7, 121.9, 118.1, 116.3, 45.6, 42.1, 41.2, 20.6, 11.2; HRMS (ES+) m/z found 406.0859; $C_{18}H_{20}N_3O_6S$ (M$^+$+H) requires 406.1073.

3,4-Dimethoxyphenyl 4-(2-oxo-3-propylimidazolidin-1-yl)benzenesulfonate. Flash chromatography (methylene chloride to methylene chloride/ethyl acetate (95:5)). Yield: 82%; White solid; mp: 139-141° C.; IR: 2932, 1705 cm$^{-1}$; $^1$H NMR (CDCl$_3$) δ 7.68-7.62 (m, 4H, Ar), 6.65-6.62 (m, 1H, Ar), 6.52-6.51 (m, 1H, Ar), 6.41-6.38 (m, 1H, Ar), 3.81-3.77 (m, 5H, CH$_2$ and CH$_3$), 3.70 (s, 3H, CH$_3$), 3.51-3.46 (m, 2H, CH$_2$), 3.25-3.20 (m, 2H, CH$_2$), 1.61-1.49 (m, 2H, CH$_2$), 0.90 (t, 3H, J=7.4 Hz, CH$_3$); $^{13}$C NMR (CDCl$_3$) δ 156.8, 149.2, 147.8, 145.9, 143.2, 129.7, 126.7, 116.1, 113.8, 110.8, 106.6, 56.0, 45.5, 42.1, 41.3, 20.6, 11.2; HRMS (ES+) m/z found 421.1191; $C_{20}H_{25}N_2O_6S$ (M$^+$+H) requires 421.1433.

3,5-Dimethoxyphenyl 4-(2-oxo-3-propylimidazolidin-1-yl)benzenesulfonate. Flash chromatography (methylene chloride to methylene chloride/ethyl acetate (80:20)). Yield: 54%; White solid; mp: 104-105° C.; IR: 1699 cm$^{-1}$, $^1$H NMR (CDCl$_3$) δ 7.76-7.66 (m, 4H, Ar), 6.29-6.28 (m, 1H, Ar), 6.14-6.13 (m, 2H, Ar), 3.83-3.78 (m, 2H, CH$_2$), 3.66 (s, 6H, 2x CH$_3$), 3.54-3.49 (m, 2H, CH$_2$), 3.28-3.23 (m, 2H, CH$_2$), 1.64-1.52 (m, 2H, CH$_2$), 0.93 (t, 3H, J=7.4 Hz, CH$_3$); $^{13}$C NMR (CDCl$_3$) δ 161.0, 156.8, 151.1, 145.9, 129.6, 127.0, 116.1, 100.8, 99.2, 55.5, 45.6, 42.1, 41.3, 20.6, 11.2; HRMS (ES+) m/z found 421.0233; $C_{20}H_{25}N_2O_6S$ (M$^+$+H) requires 421.1433.

3,4,5-Trimethoxyphenyl 4-(2-oxo-3-propylimidazolidin-1-yl)benzene sulfonate (101). Flash chromatography (methylene chloride to methylene chloride/ethyl acetate (95:5)). Yield: 63%; White solid; mp: 133-134° C.; IR: 2935, 1701 cm$^{-1}$; $^1$H NMR (CDCl$_3$) δ 7.72-7.64 (m, 4H, Ar), 6.17 (s, 2H, Ar), 3.81-3.75 (m, 2H, CH$_2$), 3.73 (s, 3H, CH$_3$), 3.65 (s, 6H, 2x CH$_3$), 3.51-3.46 (m, 2H, CH$_2$), 3.24-3.19 (m, 2H, CH$_2$), 1.61-1.49 (m, 2H, CH$_2$), 0.89 (t, 3H, J=7.4 Hz, CH$_3$); $^{13}$C NMR (CDCl$_3$) δ 156.8, 153.3, 146.0, 145.5, 136.7, 129.7, 126.7, 116.1, 100.0, 60.9, 56.2, 45.5, 42.1, 41.2, 20.6, 11.2; HRMS (ES+) m/z found 451.1385; $C_{21}H_{27}N_2O_7S$ (M$^+$+H) requires 451.1539.

p-Tolyl 4-(2-oxo-3-propylimidazolidin-1-yl)benzenesulfonate. Flash chromatography (methylene chloride to methylene chloride/ethyl acetate (95:5)). Yield: 84%; White solid; mp: 86-88° C.; IR: 2964, 1697 cm$^{-1}$; $^1$H NMR (CDCl$_3$) δ 7.66 (s, 4H, Ar), 7.02-6.99 (m, 2H, Ar), 6.81-6.78 (m, 2H, Ar), 3.82-3.77 (m, 2H, CH$_2$), 3.52-3.47 (m, 2H, CH$_2$), 3.26-3.21 (m, 2H, CH$_2$), 2.25 (s, 3H, CH$_3$), 1.62-1.51 (m, 2H, CH$_2$), 0.92 (t, 3H, J=7.3 Hz, CH$_3$); $^{13}$C NMR (CDCl$_3$) δ 156.9, 147.5, 145.8, 136.9, 130.1, 129.6, 126.8, 122.1, 116.1, 45.6, 42.1, 41.3, 20.9, 20.6, 11.2; HRMS (ES+) m/z found 375.1108; $C_{19}H_{23}N_2O_4S$ (M$^+$+H) requires 375.1379.

4-Methoxyphenyl 4-(2-oxo-3-propylimidazolidin-1-yl)benzenesulfonate. Flash chromatography (methylene chloride to methylene chloride/ethyl acetate (95:5)). Yield: 99%; White solid; mp: 105-107° C.; IR: 2967, 1696 cm$^{-1}$; $^1$H NMR (CDCl$_3$) δ 7.68 (s, 4H, Ar), 6.87-6.72 (m, 4H, Ar), 3.85-3.80 (m, 2H, CH$_2$), 3.74 (s, 3H, CH$_3$), 3.55-3.50 (m, 2H, CH$_2$), 3.29-3.24 (m, 2H, CH$_2$), 1.65-1.53 (m, 2H, CH$_2$), 0.92 (t, 3H, J=7.4 Hz, CH$_3$); $^{13}$C NMR (CDCl$_3$) δ 156.9, 147.5, 145.8, 136.9, 130.1, 129.6, 126.8, 122.1, 116.1, 45.6, 42.1, 41.3, 20.9, 20.6, 11.2; HRMS (ES+) m/z found 391.1127; $C_{19}H_{23}N_2O_5S$ (M$^+$+H) requires 391.1328.

4-Chlorophenyl 4-(2-oxo-3-propylimidazolidin-1-yl)benzenesulfonate. Flash chromatography (methylene chloride to methylene chloride/ethyl acetate (95:5)). Yield: 72%; White solid; mp: 96-98° C.; IR: 2966, 1691 cm$^{-1}$; $^1$H NMR (CDCl$_3$) δ 7.70-7.64 (m, 4H, Ar), 7.22-7.18 (m, 2H, Ar), 6.89-6.85 (m, 2H, Ar), 3.83-3.78 (m, 2H, CH$_2$), 3.53-3.48 (m, 2H, CH$_2$), 3.27-3.22 (m, 2H, CH$_2$), 1.63-1.51 (m, 2H, CH$_2$), 0.91 (t, 3H, J=7.4 Hz, CH$_3$); $^{13}$C NMR (CDCl$_3$) δ 156.8, 148.1, 146.1, 132.7, 129.7, 129.7, 126.3, 123.8, 116.2, 45.6, 42.1, 41.3, 20.6, 11.2; HRMS (ES+) m/z found 395.0851; $C_{18}H_{20}ClN_2O_4S$ (M$^+$+H) requires 395.0832.

4-Fluorophenyl 4-(2-oxo-3-propylimidazolidin-1-yl)benzenesulfonate. Flash chromatography (methylene chloride to methylene chloride/ethyl acetate (95:5)). Yield: 81%; White solid; mp: 126-127° C.; IR: 2967, 1690 cm$^{-1}$; $^1$H NMR (CDCl$_3$) δ 7.70-7.63 (m, 4H, Ar), 6.95-6.89 (m, 4H, Ar), 3.84-3.78 (m, 2H, CH$_2$), 3.54-3.48 (m, 2H, CH$_2$), 3.27-3.22 (m, 2H, CH$_2$), 1.63-1.51 (m, 2H, CH$_2$), 0.92 (t, 3H, J=7.4 Hz, CH$_3$); $^{13}$C NMR (CDCl$_3$) δ 162.6, 159.3, 156.8, 146.1, 145.5, 145.5, 129.7, 126.3, 124.1, 124.0, 116.5, 116.1, 45.6, 42.1, 41.3, 20.6, 11.2; HRMS (ES+) m/z found 379.1062; $C_{18}H_{20}FN_2O_4S$ (M$^+$+H) requires 379.1128.

3,4,5-Trimethoxyphenyl 4-(3-butyl-2-oxoimidazolidin-1-yl)benzene sulfonate (106). $^1$H NMR (CDCl$_3$) δ 7.75-7.67 (m, 4H, Ar), 6.19 (s, 2H, Ar), 3.83-3.75 (m, 5H, CH$_2$ and CH$_3$), 3.68 (s, 6H, 2xCH$_3$), 3.54-3.49 (m, 2H, CH$_2$), 3.30-3.26 (m, 2H, CH$_2$), 1.55-1.48 (m, 2H, CH$_2$), 1.37-1.30 (m, 2H, CH$_2$), 0.95-0.90 (m, 3H, CH$_3$); $^{13}$C NMR (CDCl$_3$) δ 156.8, 153.3, 145.9, 145.6, 136.8, 129.7, 126.8, 116.1, 100.0, 60.9, 56.2, 43.6, 42.1, 41.3, 29.4, 19.9, 13.7. HRMS (ES+) m/z found 465.20.

3,4,5-Trimethoxyphenyl 4-(2-oxo-3-pentylimidazolidin-1-yl)benzene sulfonate (110). $^1$H NMR (CDCl$_3$) δ 7.77-7.68 (m, 4H, Ar), 6.20 (s, 2H, Ar), 3.85-3.69 (m, 11H, CH$_2$ and 3xCH$_3$), 3.55-3.50 (m, 2H, CH$_2$), 3.31-3.26 (m, 2H, CH$_2$), 1.58-1.53 (m, 2H, CH$_2$), 1.33-1.32 (m, 4H, 2xCH$_2$), 0.91-0.87 (m, 3H, CH$_3$); $^{13}$C NMR (CDCl$_3$) δ 156.8, 153.3, 145.9, 145.6, 136.8, 129.8, 126.9, 116.1, 100.0, 60.9, 56.2, 43.9, 42.1, 41.3, 28.9, 27.0, 22.3, 14.0. HRMS (ES+) m/z found 379.1062

3,4,5-Trimethoxyphenyl 4-(3-isobutyl-2-oxoimidazolidin-1-yl)benzene sulfonate (134). $^1$H NMR (CDCl$_3$) δ 7.77-7.68 (m, 4H, Ar), 6.20 (s, 2H, Ar), 3.85-3.76 (m, 5H, CH$_2$ and CH$_3$), 3.69 (s, 6H, 2xCH$_3$), 3.55-3.50 (m, 2H, CH$_2$), 3.10-3.08 (m, 2H, CH$_2$), 1.97-1.84 (m, 1H, CH), 0.94-0.91 (m, 6H, 2xCH$_3$); $^{13}$C NMR (CDCl$_3$) δ 157.1, 153.3, 145.9, 145.6, 136.8, 129.8, 126.9, 116.2, 100.0, 60.9, 56.2, 51.7, 42.2, 42.0, 26.9, 20.0. HRMS (ES+) m/z found 465.15

Example 4

Sulfonamides (Method B)

4-(2-Oxo-3-propylimidazolidin-1-yl)-N-phenylbenzene sulfonamide. Flash chromatography (methylene chloride to methylene chloride/ethyl acetate (80:20)). Yield: 64%; White solid; mp: 179-180° C.; IR: 3162, 2964, 1685 cm$^{-1}$; $^1$H NMR (CDCl$_3$ and MeOD) δ 7.64-7.49 (m, 4H, Ar), 7.16-6.97 (m, 5H, Ar), 3.74-3.69 (m, 2H, CH$_2$), 3.47-3.42 (m, 2H, CH$_2$), 3.22-3.17 (m, 2H, CH$_2$), 2.64 (s, 1H, NH), 1.59-1.46 (m, 2H, CH$_2$), 0.87 (t, 3H, J=7.4 Hz, CH$_3$); $^{13}$C NMR (CDCl$_3$ and MeOD) δ 157.3, 144.4, 137.1, 131.5, 129.1, 128.2, 124.9, 121.4, 116.3, 45.6, 42.2, 41.4, 20.6, 11.1; HRMS (ES+) m/z found 360.1319; C$_{18}$H$_{22}$N$_3$O$_3$S (M$^+$+H) requires 360.1382.

N-(2,4-Dimethylphenyl)-4-(2-oxo-3-propylimidazolidin-1-yl) benzene sulfonamide. Flash chromatography (methylene chloride to methylene chloride/ethyl acetate (80:20)). Yield: 67%; White solid; mp: 186-188° C.; IR: 3159, 2966, 1685 cm$^{-1}$; $^1$H NMR (CDCl$_3$ and MeOD) δ 7.57-7.50 (m, 4H, Ar), 7.00-6.97 (m, 1H, Ar), 6.83-6.81 (m, 2H, Ar), 3.77-3.71 (m, 2H, CH$_2$), 3.48-3.42 (m, 2H, CH$_2$), 3.21-3.17 (m, 2H, CH$_2$), 2.77 (s, 1H, NH), 2.18 (s, 3H, CH$_3$), 1.93 (s, 3H, CH$_3$), 1.59-1.46 (m, 2H, CH$_2$), 0.88 (t, 3H, J=7.4 Hz, CH$_3$); $^{13}$C NMR (CDCl$_3$) δ 157.3, 144.4, 136.3, 132.9, 132.1, 131.8, 131.5, 128.1, 127.2, 125.7, 116.2, 45.5, 42.2, 41.3, 20.8, 20.6, 17.5, 11.1; HRMS (ES+) m/z found 388.0560; C$_{20}$H$_{26}$N$_3$O$_3$S (M$^+$+H) requires 388.1695.

N-(3-Methoxyphenyl)-4-(2-oxo-3-propylimidazolidin-1-yl)benzene sulfonamide. Flash chromatography (methylene chloride to methylene chloride/ethyl acetate (80:20)). Yield: 68%; White solid; mp: 161-162° C.; IR: 3152, 2964, 1683 cm$^{-1}$; $^1$H NMR (CDCl$_3$ and MeOD) δ 7.65-7.48 (m, 4H, Ar), 7.03-6.98 (m, 1H, Ar), 6.66 (s, 1H, Ar), 6.60-6.50 (m, 2H, Ar), 3.74-3.68 (m, 2H, CH$_2$), 3.64 (s, 3H, CH$_3$), 3.46-3.41 (m, 2H, CH$_2$), 3.20-3.15 (m, 2H, CH$_2$), 3.08 (s, 1H, NH), 1.57-1.45 (m, 2H, CH$_2$), 0.86 (t, 3H, J=7.4 Hz, CH$_3$); $^{13}$C NMR (CDCl$_3$ and MeOD) δ 160.1, 157.3, 144.4, 138.4, 131.5, 129.8, 128.2, 116.3, 113.1, 110.2, 106.7, 55.2, 45.5, 42.2, 41.3, 20.5, 11.1; HRMS (ES+) m/z found 390.1289; C$_{19}$H$_{24}$N$_3$O$_4$S (M$^+$+H) requires 390.1488.

N-(3,4-Dimethylphenyl)-4-(2-oxo-3-propylimidazolidin-1-yl)benzenesulfonamide. Flash chromatography (methylene chloride to methylene chloride/ethyl acetate (80:20)). Yield: 59%; White solid; mp: 178-179° C.; IR: 3161, 2930, 1679 cm$^{-1}$; $^1$H NMR (CDCl$_3$ and MeOD) δ 7.61-7.47 (m, 4H, Ar), 6.87-6.71 (m, 3H, Ar), 3.74-3.68 (m, 2H, CH$_2$), 3.45-3.40 (m, 2H, CH$_2$), 3.22 (s, 1H, NH), 3.20-3.15 (m, 2H, CH$_2$), 2.07 (s, 6H, 2x CH$_3$), 1.57-1.45 (m, 2H, CH$_2$), 0.86 (t, 3H, J=7.4 Hz, CH$_3$); $^{13}$C NMR (CDCl$_3$ and MeOD) δ 157.4, 144.2, 137.4, 134.5, 133.4, 131.7, 130.1, 128.2, 123.1, 119.1, 116.3, 45.5, 42.2, 41.3, 20.5, 19.6, 19.0, 11.1; HRMS (ES+) m/z found 388.1587; C$_{20}$H$_{26}$N$_3$O$_3$S (M$^+$+H) requires 388.1695.

N-(3,5-Dimethoxyphenyl)-4-(2-oxo-3-propylimidazolidin-1-yl)benzene sulfonamide (103). Flash chromatography (methylene chloride to methylene chloride/ethyl acetate (80:20)). Yield: 50%; White solid; mp: 190-192° C.; IR: 3173, 1685 cm$^{-1}$; $^1$H NMR (CDCl$_3$ and MeOD) δ 7.67-7.49 (m, 4H, Ar), 6.21-6.20 (m, 2H, Ar), 6.05 (s, 1H, Ar), 3.76-3.71 (m, 2H, CH$_2$), 3.61 (s, 6H, 2x CH$_3$), 3.46-3.41 (m, 3H, NH and CH$_2$), 3.19-3.14 (m, 2H, CH$_2$), 1.56-1.44 (m, 2H, CH$_2$), 0.85 (t, 3H, J=7.4 Hz, CH$_3$); $^{13}$C NMR (CDCl$_3$ and MeOD) δ 161.0, 157.3, 144.4, 139.1, 131.6, 128.2, 116.3, 98.7, 96.5, 55.2, 45.5, 42.2, 41.3, 20.5, 11.0; HRMS (ES+) m/z found 420.1300; C$_{20}$H$_{26}$N$_3$O$_5$S (M$^+$+H) requires 420.1593.

4-(2-Oxo-3-propylimidazolidin-1-yl)-N-(3,4,5-trimethoxyphenyl) benzene sulfonamide (102). Flash chromatography (methylene chloride to methylene chloride/ethyl acetate (50:50)). Yield: 59%; White solid; mp: 166-168° C.; IR: 3116, 2961, 1678 cm$^{-1}$; $^1$H NMR (CDCl$_3$ and MeOD) δ 7.59-7.45 (m, 4H, Ar), 6.27 (s, 2H, Ar), 3.74-3.65 (m, 2H, CH$_2$), 3.62 (s, 3H, CH$_3$), 3.59 (s, 6H, 2x CH$_3$), 3.42-3.37 (m, 3H, CH$_2$ and NH), 3.15-3.10 (m, 2H, CH$_2$), 1.52-1.40 (m, 2H, CH$_2$), 0.81 (t, 3H, J=7.4 Hz, CH$_3$); $^{13}$C NMR (CDCl$_3$ and MeOD) δ 157.3, 153.2, 144.4, 134.9, 133.3, 131.4, 128.2, 116.2, 99.0, 60.7, 55.9, 45.5, 42.1, 41.3, 20.5, 11.0; HRMS (ES+) m/z found 450.1531; C$_{21}$H$_{28}$N$_3$O$_6$S (M$^+$+H) requires 450.1699.

N-(4-Fluorophenyl)-4-(2-oxo-3-propylimidazolidin-1-yl) benzene sulfonamide. Flash chromatography (methylene chloride to methylene chloride/ethyl acetate (80:20)). Yield: 63%; White solid; mp: 166-168° C.; IR: 3191, 2965, 1686 cm-1; 1H NMR (CDCl$_3$ and MeOD) δ 7.47-7.39 (m, 4H, Ar), 6.88-6.84 (m, 2H, Ar), 6.73-6.68 (m, 2H, Ar), 3.68-3.63 (m, 2H, CH$_2$), 3.38-3.33 (m, 2H, CH$_2$), 3.09-3.04 (m, 2H, CH$_2$), 1.47-1.35 (m, 2H, CH$_2$), 0.76 (t, 3H, J=7.4 Hz, CH$_3$); $^{13}$C NMR (CDCl$_3$ and MeOD) δ 161.7, 158.5, 157.4, 144.2, 133.1, 133.0, 131.3, 128.0, 124.0, 123.9, 116.3, 115.7, 115.4, 45.3, 42.1, 41.2, 20.3, 10.8; HRMS (ES+) m/z found 378.0579; C$_{15}$H$_{21}$FN$_3$O$_3$S (M$^+$+H) requires 378.1288.

Example 5

Antiproliferative Activity on HT-29, M21 and MCF-7, MDA-MB-231, MDA-MB-468 and T47D Cells Inhibition of tumor cell growth inhibition activity of the compounds of the invention was evaluated on six human cell lines: four breast carcinoma cell lines: MCF-7, MDA-MB-231, MDA-MB-468, and T47D, skin melanoma: M21, colon carcinoma: HT-29 and fibrosarcoma: HT-1080. Cell growth inhibition was assessed according to the NCI/NIH Developmental Therapeutics Program with slight modifications. The GI$_{50}$ is the concentration of the drug decreasing by 50% the proliferation of the tumor cells tested.

Tumor Cell Growth Inhibition Assay.

The growth inhibition potency of these compounds was assessed using the procedure described by the National Cancer Institute for its drug screening program. Ninety six-well microtiter plates were seeded with 100 μL of tumor cell lines in calf serum iron supplemented (Hyclone) medium. Plates were incubated at 37° C., 5% CO$_2$ for 24 h. Freshly solubilized drugs in DMSO were diluted in fresh medium and aliquots of 100 μL containing sequential dilution of drugs were added. DMSO concentration was maintained lower than 0.5% to avoid toxicity. Plates were incubated for 48 h or 72 h depending of cell growth rates. Assays were stopped by addition of cold trichloroacetic acid to the wells (10% final concentration), followed by incubation for 1 h at 4° C. Plates were washed five times with water. Sulforhodamine B solution (50 μL) at 0.1% (w/v) in 1% acetic acid was added to each well, and plates were incubated for 15 min at room temperature. After staining, unbound dye was removed by washing five times with 1% acetic acid. Bonded dye was solubilized with 10 mM Tris base, and the absorbance was read using a Quant Universal Microplate Spectrophotometer (Biotek, Winooski, Vt.) at 585 nm. A background OD from a control reference plate fixed on the day of treatment was subtracted from the OD obtained with the 48 h or 72 h growth period. The growth inhibition percentage was calculated in reference to the control DMSO-treated cells for each drug concentration. The experiments were performed at least twice in triplicate. The $IG_{50}$ assay was considered valid when the variability among data for a given set of conditions, within the same experiment, was less than 10% with respect to the mean value.

As will be well understood by persons of skill in the art, a high ratio of $GI_{50}$ inhibition activity on sensitive cell lines: MCF-7, MDA-MB-468 or T47D compared to non-sensitive cell lines: M21, HT-29, HT-1080 or MDA-MB-231 is a strong indication that the compounds are highly selective for at least certain types of cancer cells, for example but not limited to, breast cancer cells. This provides advantageous compounds for treating certain types of cancer with minimal activity to other cells of the body, thereby providing anti-cancer drugs with high activity and low toxicity (i.e. selectivity).

All compounds presented in the Table 1 were found to be active in at least one of the above-mentioned cell line assay with a $GI_{50}$ equal or below $10^{-4}$ M and have a ratio of selectivity (i.e. non-sensitive cancer cell line/sensitive cell line) about or greater than 10.

TABLE 1

| cpd # | Structures | Name | MS |
|---|---|---|---|
| 101 | 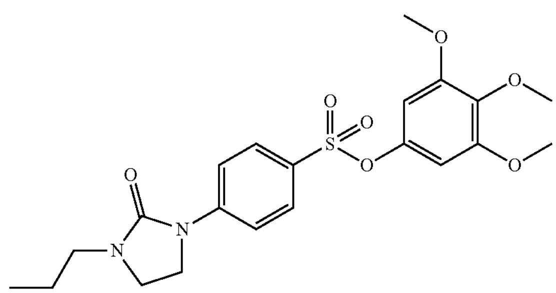 [SMILES: CCCN1CCN(c2ccc(S(=O)(=O)Oc3cc(OC)c(OC)c(OC)c3)cc2)C1=O] | 3,4,5-trimethoxyphenyl 4-(2-oxo-3-propylimidazolidin-1-yl)benzenesulfonate | 451.15 |
| 102 | 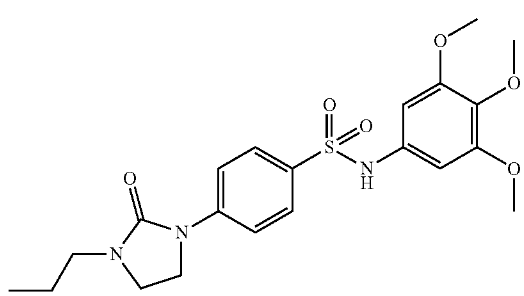 [SMILES: CCCN1CCN(c2ccc(S(=O)(=O)Nc3cc(OC)c(OC)c(OC)c3)cc2)C1=O] | 4-(2-oxo-3-propyl-imidazolidin-1-yl)-N-(3,4,5-trimethoxy-phenyl)-benzenesulfonamide | 450.15 |
| 103 | 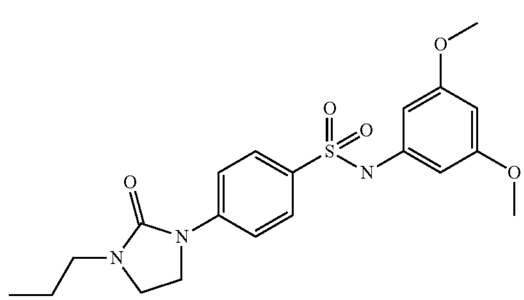 [SMILES: CCCN1CCN(c2ccc(S(=O)(=O)Nc3cc(OC)cc(OC)c3)cc2)C1=O] | N-(3,5-Dimethoxy-phenyl)-4-(2-oxo-3-propyl-imidazolidin-1-yl)-benzenesulfonamide | 420.15 |

TABLE 1-continued

| cpd # | Structures | Name | MS |
|---|---|---|---|
| 104 | 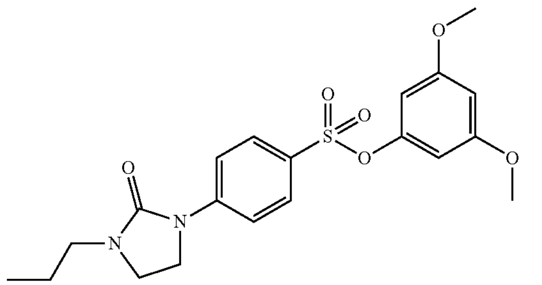 [SMILES: CCCN1CCN(c2ccc(S(=O)(=O)Oc3cc(OC)cc(OC)c3)cc2)C1=O] | 3,5-dimethoxyphenyl 4-(2-oxo-3-propylimidazolidin-1-yl)benzenesulfonate | 421.15 |
| 105 | 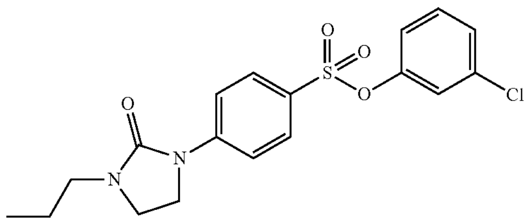 [SMILES: CCCN1CCN(c2ccc(S(=O)(=O)Oc3cccc(Cl)c3)cc2)C1=O] | 3-chlorophenyl 4-(2-oxo-3-propylimidazolidin-1-yl)benzenesulfonate | 395.05 |
| 106 | 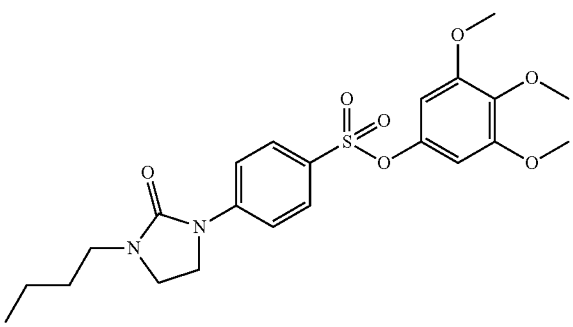 [SMILES: CCCCN1CCN(c2ccc(S(=O)(=O)Oc3cc(OC)c(OC)c(OC)c3)cc2)C1=O] | 3,4,5-trimethoxyphenyl 4-(3-butyl-2-oxoimidazolidin-1-yl)benzenesulfonate | 465.20 |
| 107 | 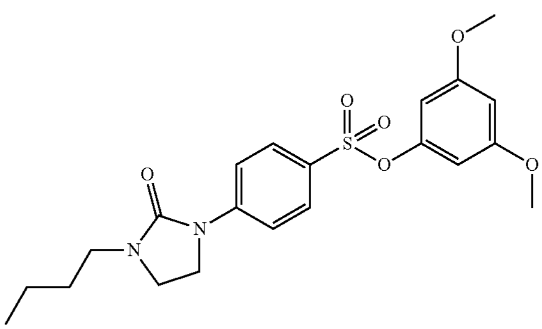 [SMILES: CCCCN1CCN(c2ccc(S(=O)(=O)Oc3cc(OC)cc(OC)c3)cc2)C1=O] | 3,5-dimethoxyphenyl 4-(3-butyl-2-oxoimidazolidin-1-yl)benzenesulfonate | 435.15 |
| 108 | 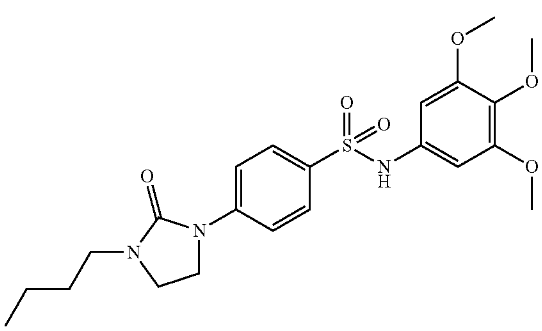 [SMILES: CCCCN1CCN(c2ccc(S(=O)(=O)Nc3cc(OC)c(OC)c(OC)c3)cc2)C1=O] | 4-(3-Butyl-2-oxo-imidazolidin-1-yl)-N-(3,4,5-trimethoxy-phenyl)-benzenesulfonamide | 464.20 |

TABLE 1-continued

| cpd # | Structures | Name | MS |
|---|---|---|---|
| 109 | 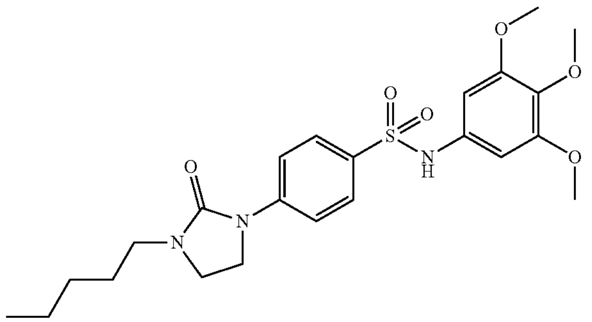 [SMILES: CCCCCN1CCN(c2ccc(S(=O)(=O)Nc3cc(OC)c(OC)c(OC)c3)cc2)C1=O] | 4-(2-Oxo-3-pentyl-imidazolidin-1-yl)-N-(3,4,5-trimethoxy-phenyl)-benzenesulfonamide | 478.20 |
| 110 | 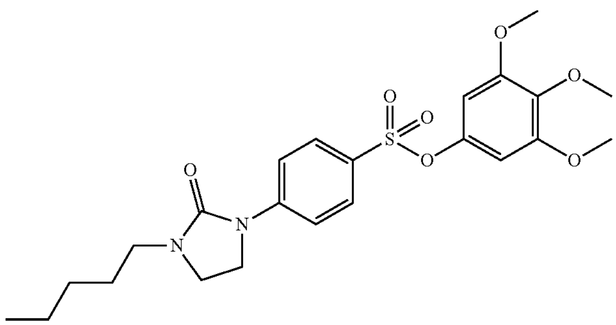 [SMILES: CCCCCN1CCN(c2ccc(S(=O)(=O)Oc3cc(OC)c(OC)c(OC)c3)cc2)C1=O] | 3,4,5-trimethoxyphenyl 4-(2-oxo-3-pentylimidazolidin-1-yl)benzenesulfonate | 479.20 |
| 111 | 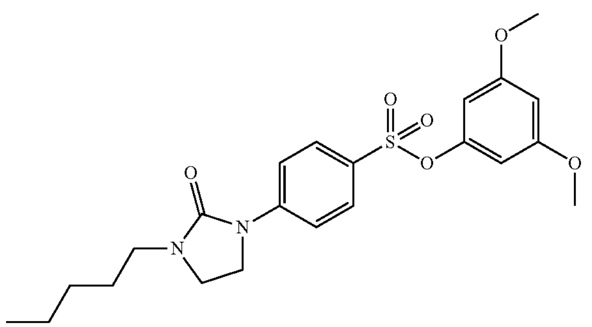 [SMILES: CCCCCN1CCN(c2ccc(S(=O)(=O)Oc3cc(OC)cc(OC)c3)cc2)C1=O] | 3,5-dimethoxyphenyl 4-(2-oxo-3-pentylimidazolidin-1-yl)benzenesulfonate | 449.15 |
| 112 | 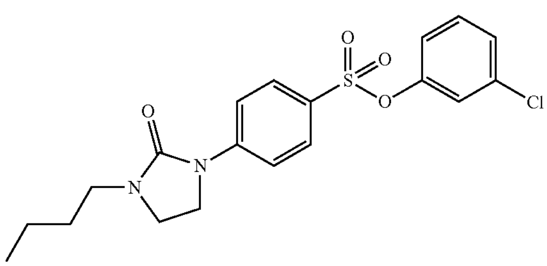 [SMILES: CCCCN1CCN(c2ccc(S(=O)(=O)Oc3cccc(Cl)c3)cc2)C1=O] | 3-chlorophenyl 4-(3-butyl-2-oxoimidazolidin-1-yl)benzenesulfonate | 409.10 |
| 113 | 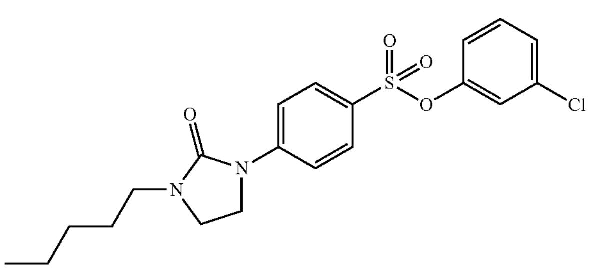 [SMILES: CCCCCN1CCN(c2ccc(S(=O)(=O)Oc3cccc(Cl)c3)cc2)C1=O] | 3-chlorophenyl 4-(2-oxo-3-pentylimidazolidin-1-yl)benzenesulfonate | 423.10 |

TABLE 1-continued

| cpd # | Structures | Name | MS |
|---|---|---|---|
| 114 | 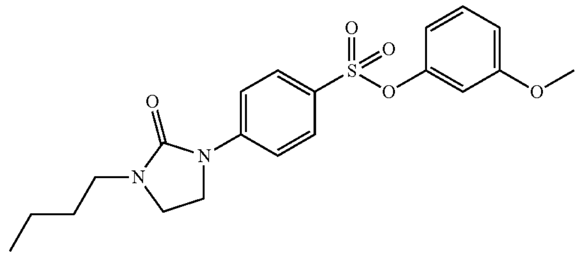 [SMILES: CCCCN1CCN(c2ccc(S(=O)(=O)Oc3cccc(OC)c3)cc2)C1=O] | 3-methoxyphenyl 4-(3-butyl-2-oxoimidazolidin-1-yl)benzenesulfonate | 405.15 |
| 115 | 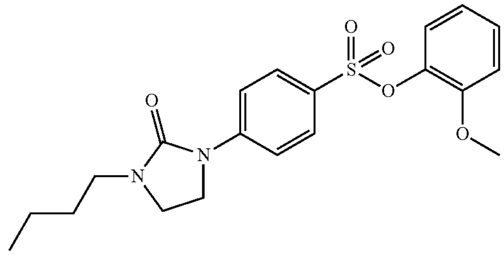 [SMILES: CCCCN1CCN(c2ccc(S(=O)(=O)Oc3ccccc3OC)cc2)C1=O] | 2-methoxyphenyl 4-(3-butyl-2-oxoimidazolidin-1-yl)benzenesulfonate | 405.15 |
| 116 | 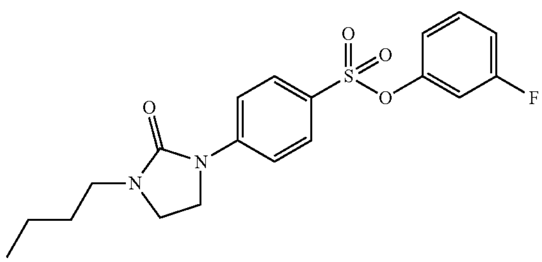 [SMILES: CCCCN1CCN(c2ccc(S(=O)(=O)Oc3cccc(F)c3)cc2)C1=O] | 3-fluorophenyl 4-(3-butyl-2-oxoimidazolidin-1-yl)benzenesulfonate | 393.10 |
| 117 | 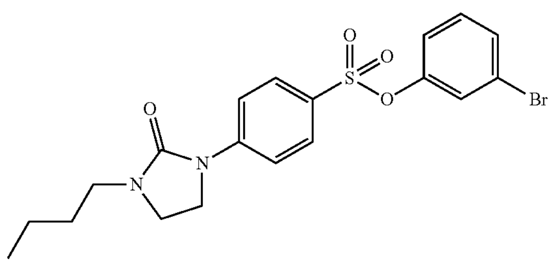 [SMILES: CCCCN1CCN(c2ccc(S(=O)(=O)Oc3cccc(Br)c3)cc2)C1=O] | 3-bromophenyl 4-(3-butyl-2-oxoimidazolidin-1-yl)benzenesulfonate | 453.05 |
| 118 | 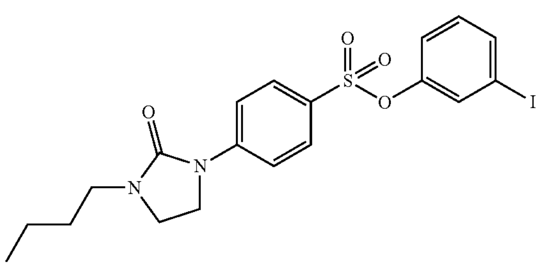 [SMILES: CCCCN1CCN(c2ccc(S(=O)(=O)Oc3cccc(I)c3)cc2)C1=O] | 3-iodophenyl 4-(3-butyl-2-oxoimidazolidin-1-yl)benzenesulfonate | 501.05 |
| 119 | 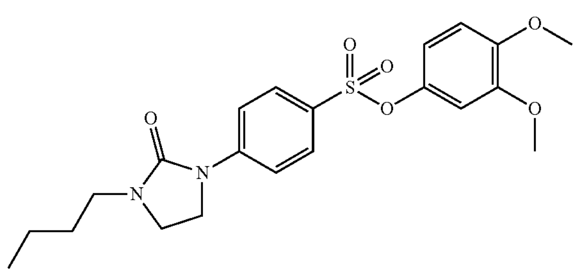 [SMILES: CCCCN1CCN(c2ccc(S(=O)(=O)Oc3ccc(OC)c(OC)c3)cc2)C1=O] | 3,4-dimethoxyphenyl 4-(3-butyl-2-oxoimidazolidin-1-yl)benzenesulfonate | 435.20 |

TABLE 1-continued

| cpd # | Structures | Name | MS |
|---|---|---|---|
| 120 | 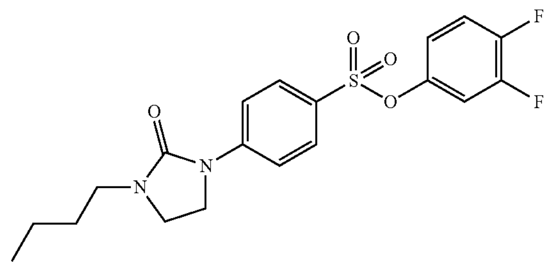 [SMILES: CCCCN1CCN(c2ccc(S(=O)(=O)Oc3ccc(F)c(F)c3)cc2)C1=O] | 3,4-difluorophenyl 4-(3-butyl-2-oxoimidazolidin-1-yl)benzenesulfonate | 411.15 |
| 121 | 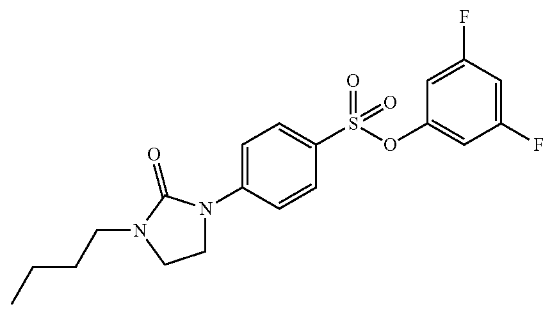 [SMILES: CCCCN1CCN(c2ccc(S(=O)(=O)Oc3cc(F)cc(F)c3)cc2)C1=O] | 3,5-difluorophenyl 4-(3-butyl-2-oxoimidazolidin-1-yl)benzenesulfonate | 411.15 |
| 122 | 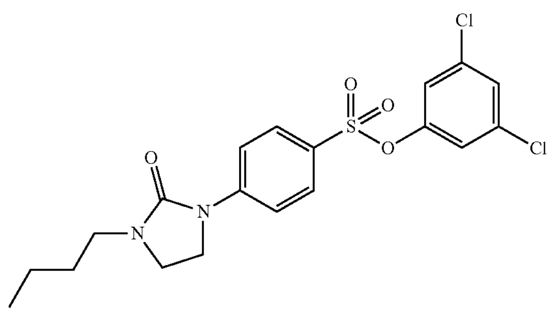 [SMILES: CCCCN1CCN(c2ccc(S(=O)(=O)Oc3cc(Cl)cc(Cl)c3)cc2)C1=O] | 3,5-dichlorophenyl 4-(3-butyl-2-oxoimidazolidin-1-yl)benzenesulfonate | 443.05 |
| 123 | 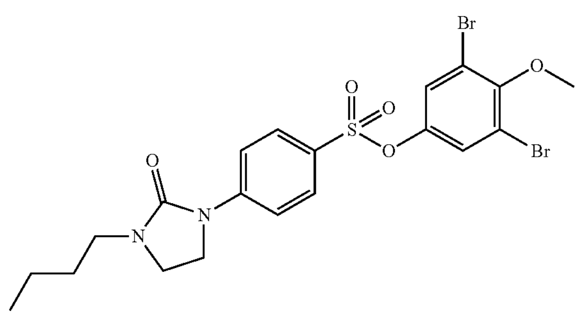 [SMILES: CCCCN1CCN(c2ccc(S(=O)(=O)Oc3cc(Br)c(OC)c(Br)c3)cc2)C1=O] | 3,5-dibromo-4-methoxyphenyl 4-(3-butyl-2-oxoimidazolidin-1-yl)benzenesulfonate | 561.00 |
| 124 | 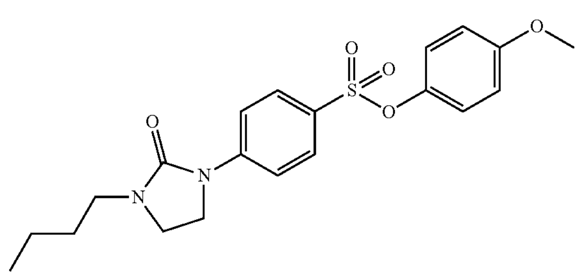 [SMILES: CCCCN1CCN(c2ccc(S(=O)(=O)Oc3ccc(OC)cc3)cc2)C1=O] | 4-methoxyphenyl 4-(3-butyl-2-oxoimidazolidin-1-yl)benzenesulfonate | 405.15 |

TABLE 1-continued
| cpd # | Structures | Name | MS |
|---|---|---|---|
| 125 | 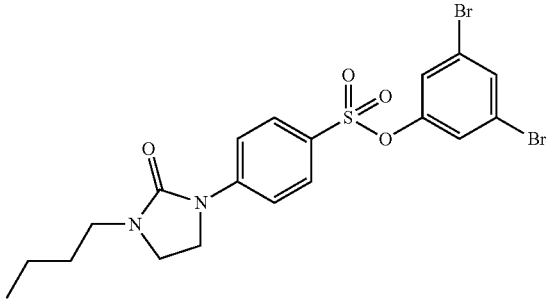 [SMILES: CCCCN1CCN(c2ccc(S(=O)(=O)Oc3cc(Br)cc(Br)c3)cc2)C1=O] | 3,5-dibromophenyl 4-(3-butyl-2-oxoimidazolidin-1-yl)benzenesulfonate | 530.95 |
| 126 | 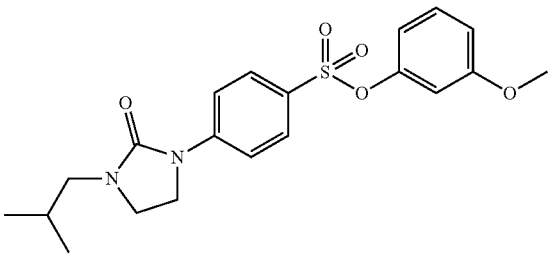 [SMILES: COc1cccc(OS(=O)(=O)c2ccc(N3CCN(CC(C)C)C3=O)cc2)c1] | 3-methoxyphenyl 4-(3-isobutyl-2-oxoimidazolidin-1-yl)benzenesulfonate | 405.15 |
| 127 | 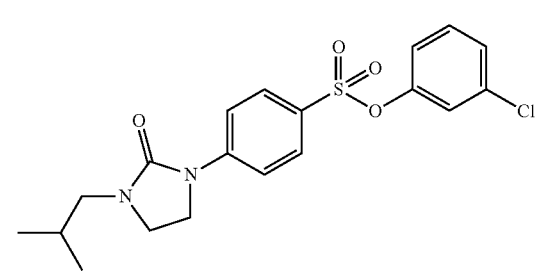 [SMILES: CC(C)CN1CCN(c2ccc(S(=O)(=O)Oc3cccc(Cl)c3)cc2)C1=O] | 3-chlorophenyl 4-(3-isobutyl-2-oxoimidazolidin-1-yl)benzenesulfonate | 409.10 |
| 128 | 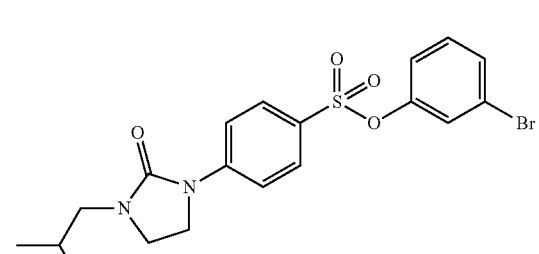 | 3-bromophenyl 4-(3-isobutyl-2-oxoimidazolidin-1-yl)benzenesulfonate | 453.05 |
| 129 | 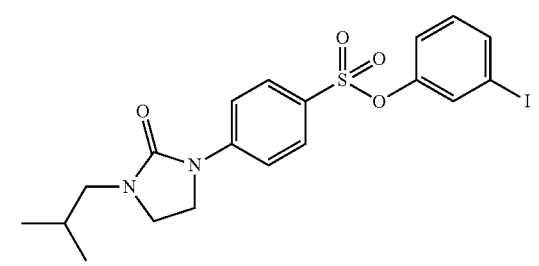 [SMILES: CC(C)CN1CCN(c2ccc(S(=O)(=O)Oc3cccc(I)c3)cc2)C1=O] | 3-iodophenyl 4-(3-isobutyl-2-oxoimidazolidin-1-yl)benzenesulfonate | 501.05 |

TABLE 1-continued

| cpd # | Structures | Name | MS |
|---|---|---|---|
| 130 | 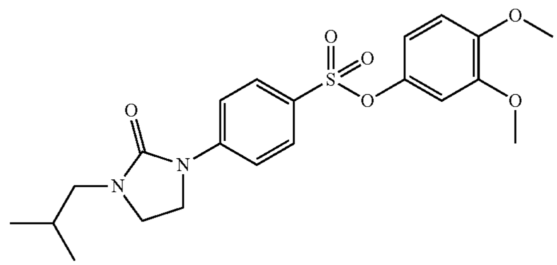 [SMILES: COc1ccc(OS(=O)(=O)c2ccc(N3CCN(CC(C)C)C3=O)cc2)cc1OC] | 3,4-dimethoxyphenyl 4-(3-isobutyl-2-oxoimidazolidin-1-yl)benzenesulfonate | 435.05 |
| 131 | 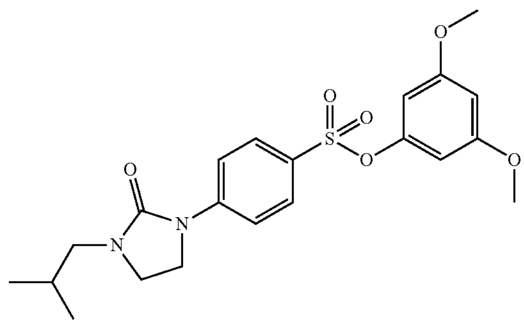 [SMILES: COc1cc(OC)cc(OS(=O)(=O)c2ccc(N3CCN(CC(C)C)C3=O)cc2)c1] | 3,5-dimethoxyphenyl 4-(3-isobutyl-2-oxoimidazolidin-1-yl)benzenesulfonate | 435.20 |
| 132 | 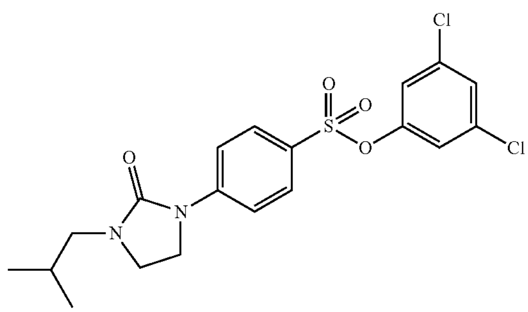 | 3,5-dichlorophenyl 4-(3-isobutyl-2-oxoimidazolidin-1-yl)benzenesulfonate | 443.05 |
| 133 | 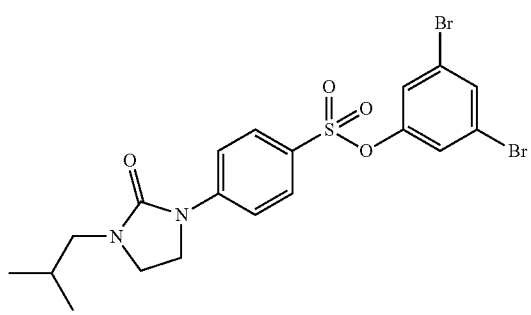 [SMILES: CC(C)CN1CCN(c2ccc(S(=O)(=O)Oc3cc(Br)cc(Br)c3)cc2)C1=O] | 3,5-dibromophenyl 4-(3-isobutyl-2-oxoimidazolidin-1-yl)benzenesulfonate | 531.00 |
| 134 | 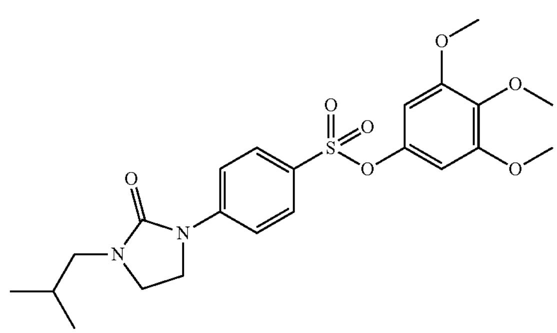 [SMILES: COc1cc(OS(=O)(=O)c2ccc(N3CCN(CC(C)C)C3=O)cc2)cc(OC)c1OC] | 3,4,5-trimethoxyphenyl 4-(3-isobutyl-2-oxoimidazolidin-1-yl)benzenesulfonate | 465.15 |

TABLE 1-continued
| cpd # | Structures | Name | MS |
|---|---|---|---|
| 135 | 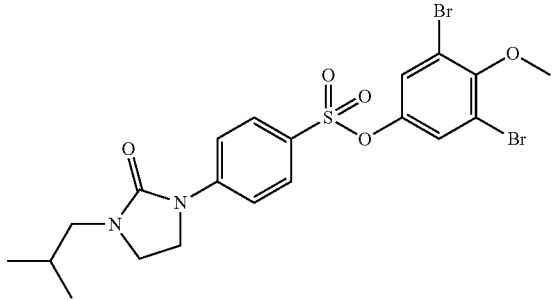 [SMILES: COc1c(Br)cc(OS(=O)(=O)c2ccc(N3CCN(CC(C)C)C3=O)cc2)cc1Br] | 3,5-dibromo-4-methoxyphenyl 4-(3-isobutyl-2-oxoimidazolidin-1-yl)benzenesulfonate | 561.05 |
| 136 | 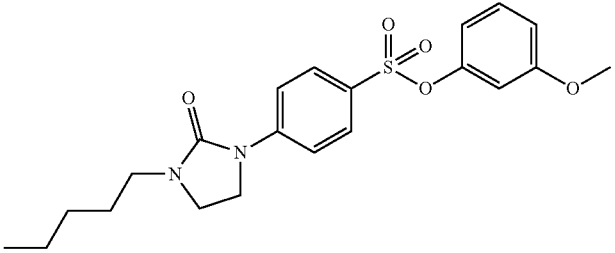 [SMILES: CCCCCN1CCN(c2ccc(S(=O)(=O)Oc3cccc(OC)c3)cc2)C1=O] | 3-methoxyphenyl 4-(2-oxo-3-pentylimidazolidin-1-yl)benzenesulfonate | 419.15 |
| 137 | 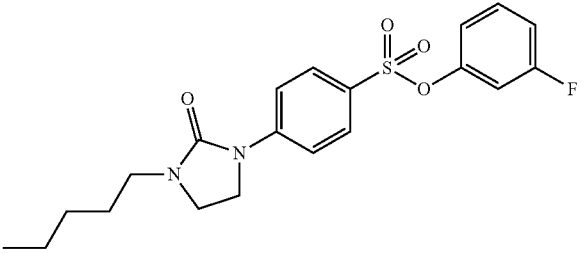 [SMILES: CCCCCN1CCN(c2ccc(S(=O)(=O)Oc3cccc(F)c3)cc2)C1=O] | 3-fluorophenyl 4-(2-oxo-3-pentylimidazolidin-1-yl)benzenesulfonate | 407.10 |
| 138 | 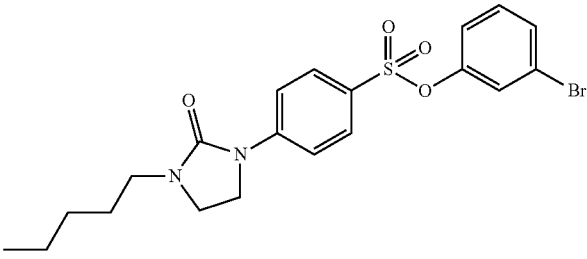 [SMILES: CCCCCN1CCN(c2ccc(S(=O)(=O)Oc3cccc(Br)c3)cc2)C1=O] | 3-bromophenyl 4-(2-oxo-3-pentylimidazolidin-1-yl)benzenesulfonate | 467.05 |
| 139 | 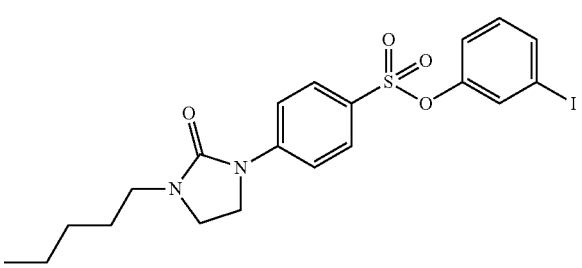 [SMILES: CCCCCN1CCN(c2ccc(S(=O)(=O)Oc3cccc(I)c3)cc2)C1=O] | 3-iodophenyl 4-(2-oxo-3-pentylimidazolidin-1-yl)benzenesulfonate | 515.10 |

TABLE 1-continued

| cpd # | Structures | Name | MS |
|---|---|---|---|
| 140 | 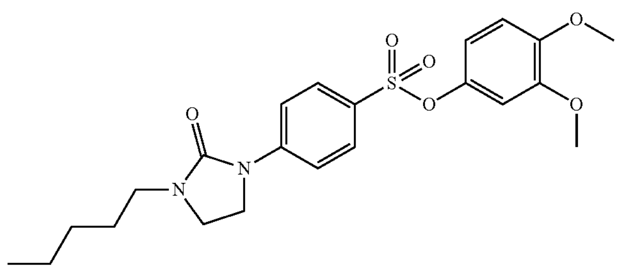 [SMILES: CCCCCN1CCN(c2ccc(S(=O)(=O)Oc3ccc(OC)c(OC)c3)cc2)C1=O] | 3,4-dimethoxyphenyl 4-(2-oxo-3-pentylimidazolidin-1-yl)benzenesulfonate | 449.15 |
| 141 | 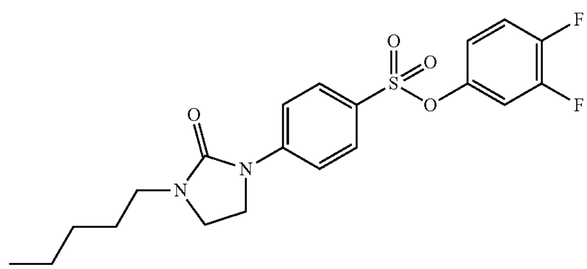 [SMILES: CCCCCN1CCN(c2ccc(S(=O)(=O)Oc3ccc(F)c(F)c3)cc2)C1=O] | 3,4-difluorophenyl 4-(2-oxo-3-pentylimidazolidin-1-yl)benzenesulfonate | 425.10 |
| 142 | 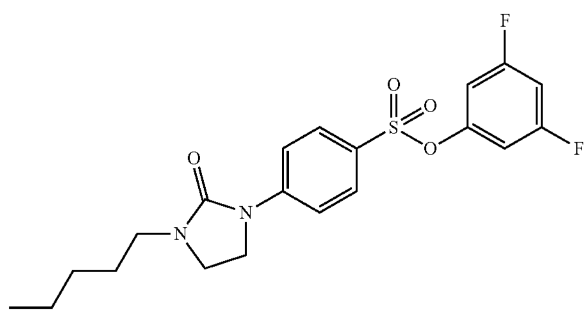 [SMILES: CCCCCN1CCN(c2ccc(S(=O)(=O)Oc3cc(F)cc(F)c3)cc2)C1=O] | 3,5-difluorophenyl 4-(2-oxo-3-pentylimidazolidin-1-yl)benzenesulfonate | 425.10 |
| 143 | 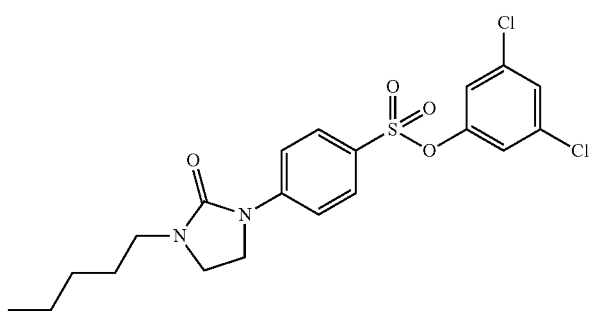 [SMILES: CCCCCN1CCN(c2ccc(S(=O)(=O)Oc3cc(Cl)cc(Cl)c3)cc2)C1=O] | 3,5-dichlorophenyl 4-(2-oxo-3-pentylimidazolidin-1-yl)benzenesulfonate | 457.05 |
| 144 | 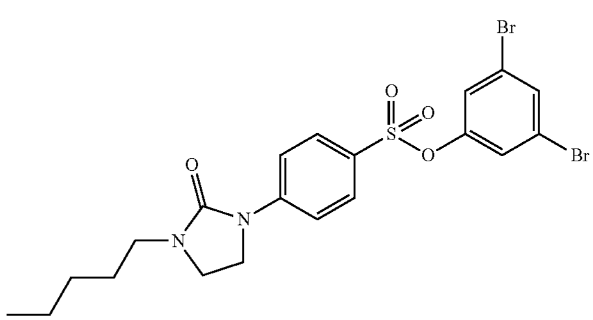 [SMILES: CCCCCN1CCN(c2ccc(S(=O)(=O)Oc3cc(Br)cc(Br)c3)cc2)C1=O] | 3,5-dibromophenyl 4-(2-oxo-3-pentylimidazolidin-1-yl)benzenesulfonate | 545.00 |

The invention claimed is:

1. A method of treating cancer by hindering or blocking cell cycle progression, said method comprising administering a therapeutically effective amount of a composition comprising at least one compound of formula (I):

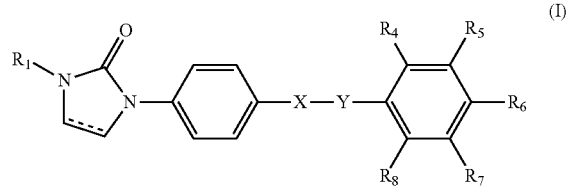

wherein:
imidazo ring is saturated or unsaturated;
$R_1$ is an unsubstituted $C_{3-8}$ linear or branched alkyl;
X is O or NH when $Y=SO_2$; and $X=SO_2$ when Y is O or NH;
or X is —CH=CH— and Y is C=O;
or X is C=O, —S— or $C=CH_2$; and Y is absent;
$R_4$ and $R_8$ is each independently selected from the group consisting of: H, OH, halogen, unsubstituted $C_{1-6}$ alkyl and unsubstituted $C_{1-6}$ alkoxy;
$R_5$, $R_6$ and $R_7$ is each independently selected from the group consisting of: H, OH, halogen, unsubstituted $C_{1-6}$ alkyl and unsubstituted $C_{1-6}$ alkoxy, provided that at least one of $R_4$, $R_5$, $R_6$, $R_7$ or $R_8$ is not H;
or a pharmaceutically acceptable derivative or salt thereof;
in admixture with at least one pharmaceutically-acceptable excipient, to a patient suffering from said cancer, wherein the cancer is gastrointestinal cancer, lung cancer, ovarian cancer, prostate cancer, breast cancer, uterine cancer, or cervical cancer.

2. The method of claim 1, comprising the compound of formula (I) wherein:
$R_1$ is n-propyl, n-butyl, isobutyl, n-pentyl, isopentyl, 2,2-dimethylbutyl or n-hexyl;
X is O or NH when $Y=SO_2$; and $X=SO_2$ when Y is O or NH;
or X is —CH=CH— and Y is C=O;
or X is C=O, —S— or $C=CH_2$; and Y is absent;
$R_4$ and $R_8$ is each independently selected from the group consisting of: H, OH, halogen, unsubstituted $C_{1-6}$ alkyl and unsubstituted $C_{1-6}$ alkoxy;
$R_5$, $R_6$ and $R_7$ is each independently selected from the group consisting of: H, OH, halogen, unsubstituted $C_{1-6}$ alkyl and unsubstituted $C_{1-6}$ alkoxy, provided that at least one of $R_4$, $R_5$, $R_6$, $R_7$ or $R_8$ is not H;
or a pharmaceutically acceptable derivative or salt thereof.

3. The method of claim 2, comprising the compound of formula (Ia) wherein:

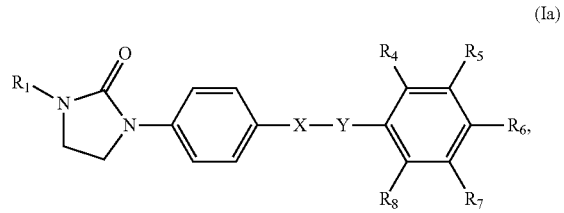

wherein:
$R_1$ is n-propyl, n-butyl, isobutyl, n-pentyl, isopentyl, 2,2-dimethylbutyl or n-hexyl;
X is O or NH when $Y=SO_2$; and $X=SO_2$ when Y is O or NH;
$R_4$ and $R_8$ is each independently selected from the group consisting of: H, OH, halogen, unsubstituted $C_{1-4}$ alkyl and unsubstituted $C_{1-6}$ alkoxy;
$R_5$, $R_6$ and $R_7$ is each independently selected from the group consisting of: H, OH, halogen, unsubstituted $C_{1-4}$ alkyl and unsubstituted $C_{1-4}$ alkoxy, provided that at least one of $R_4$, $R_5$, $R_6$, $R_7$ or $R_8$ is not H;
or a pharmaceutically acceptable derivative or salt thereof.

4. The method of claim 3, comprising the compound of formula (Ia) wherein:
$R_1$ is n-propyl, n-butyl, isobutyl, n-pentyl, isopently or n-hexyl;
$X=SO_2$ when Y is O or NH;
$R_4$ and $R_8$ are H;
$R_5$, $R_6$ and $R_7$ is each independently selected from the group consisting of: H, halogen and unsubstituted $C_{1-3}$ alkoxy, provided that at least one of $R_4$, $R_5$, $R_6$, $R_7$ or $R_8$ is not H;
or a pharmaceutically acceptable derivative or salt thereof.

5. The method of claim 1, comprising the compound of formula (I)
wherein:
$R_1$ is n-propyl, n-butyl, isobutyl or n-pentyl; X is O or NH when $Y=SO_2$; and $X=SO_2$ when Y is O or NH; $R_4$ is H and $R_8$ is H; $R_5$, $R_6$ and $R_7$ is each independently selected from the group consisting of: H, halo, and unsubstituted $C_{1-3}$ alkoxy, provided that at least one of $R_5$, $R_6$ and $R_7$ is not H, or a pharmaceutically acceptable derivative or salt thereof.

6. The method of claim 1, comprising the compound of formula (Ib):

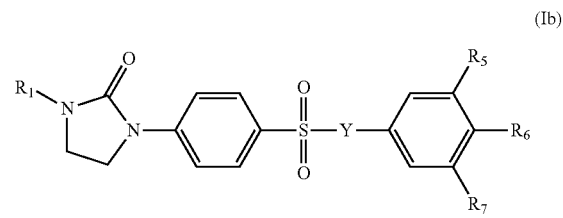

wherein $R_1$ is n-propyl, n-butyl, isobutyl or n-pentyl; $Y=O$ or NH; $R_5$, $R_6$ and $R_7$ is each independently selected from the group consisting of: H, Cl, I, Br, F, and OMe, provided that at least one of $R_5$, $R_6$ and $R_7$ is not H, or a pharmaceutically acceptable derivative or salt thereof.

7. The method of claim 6, comprising the compound of formula (Ib) wherein $R_1$ is n-butyl, isobutyl or n-pentyl; $Y=O$ or NH; $R_5$, $R_6$ and $R_7$ is each independently selected from the group consisting of: H, Cl, I, Br, F, and OMe, provided that at least one of $R_5$, $R_6$ and $R_7$ is not H, or a pharmaceutically acceptable derivative or salt thereof.

8. The method of claim 7, wherein the compound of formula (Ib) is selected from the group consisting of:

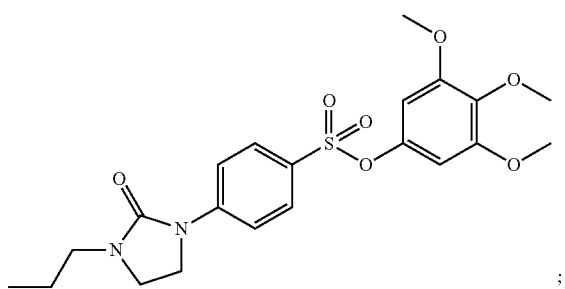
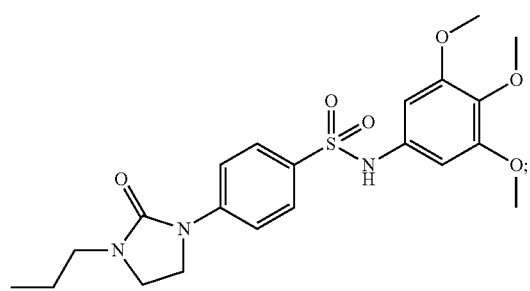
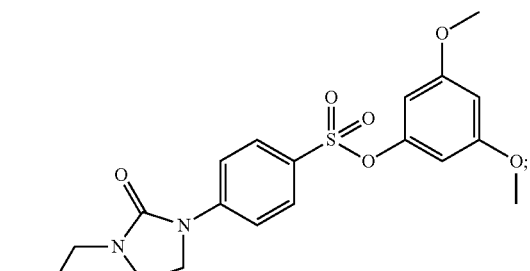
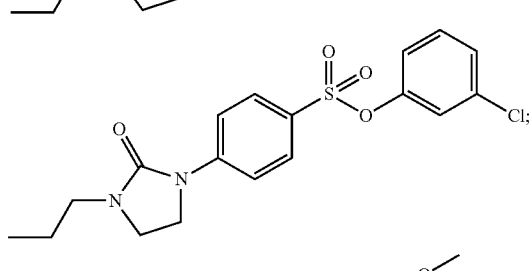
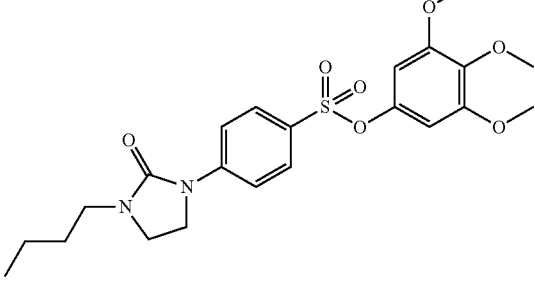
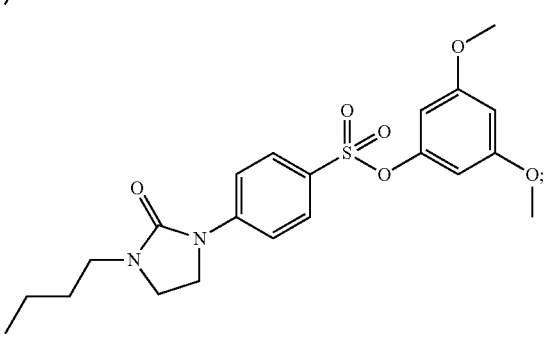
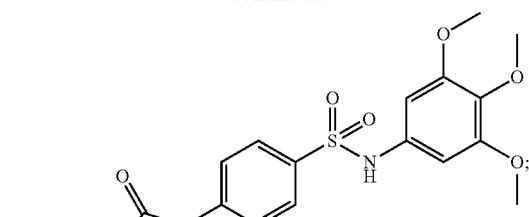
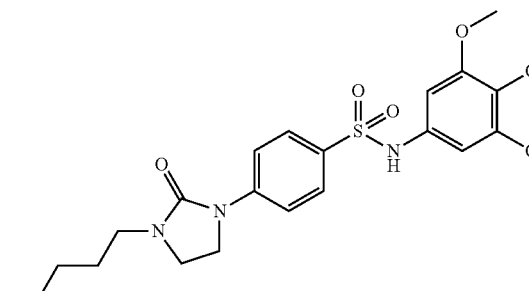
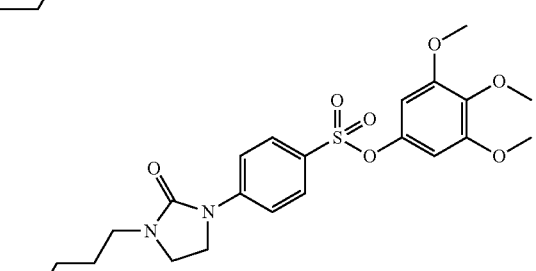
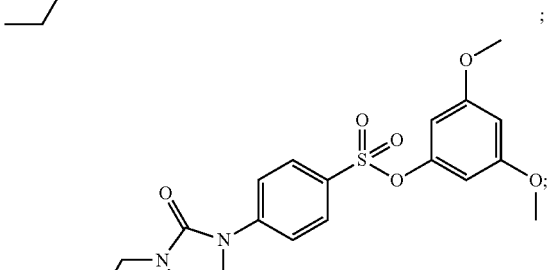
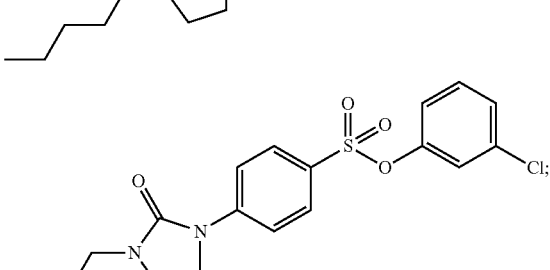
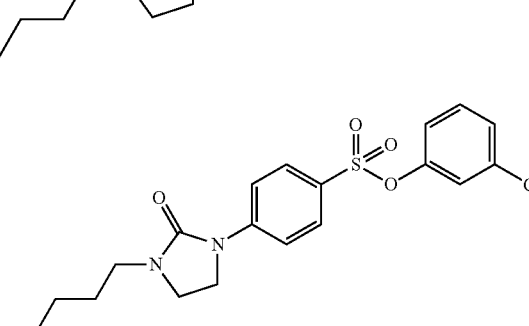

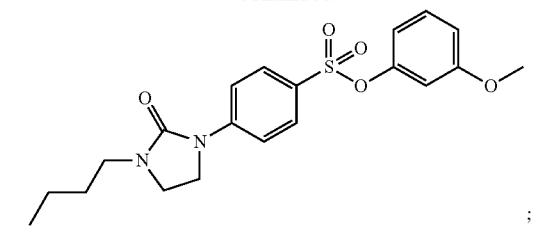
;
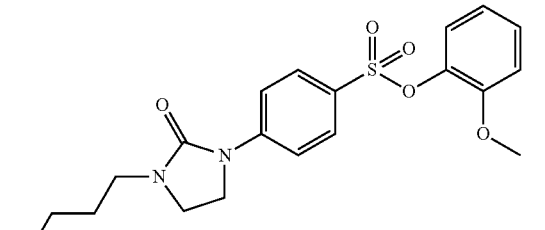
;
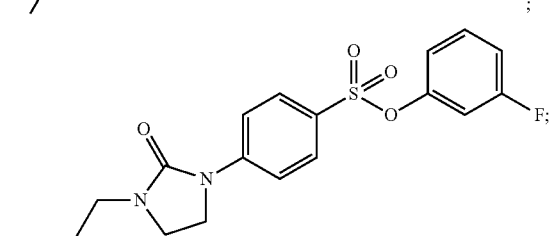
;
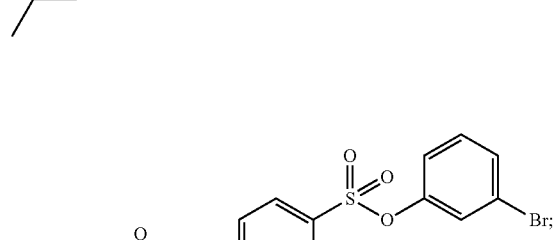
;
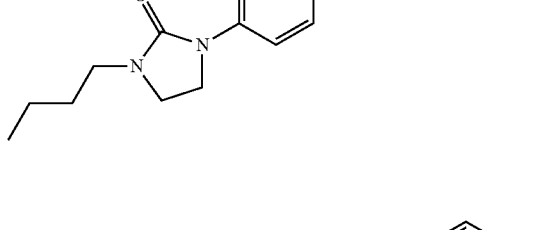
;
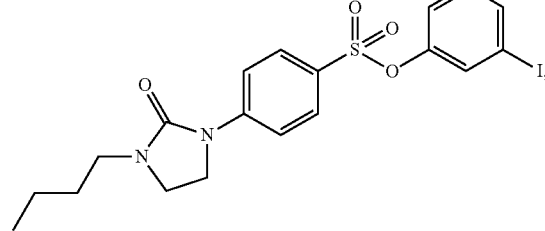
;
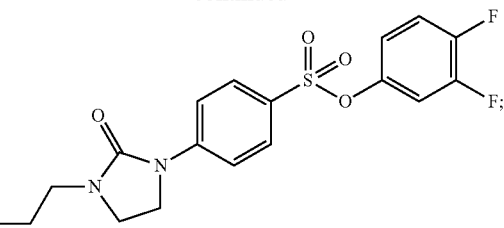
;
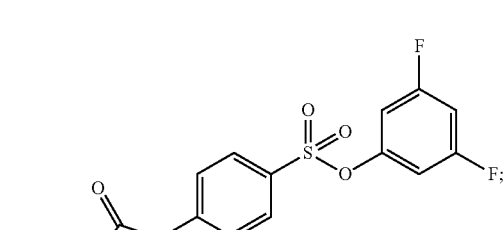
;
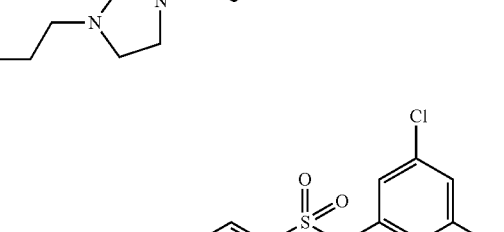
;
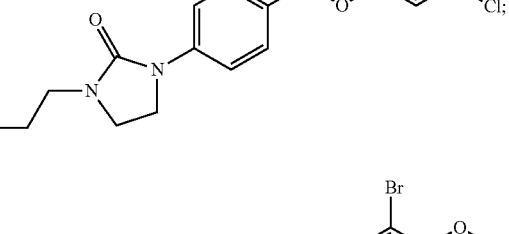
;
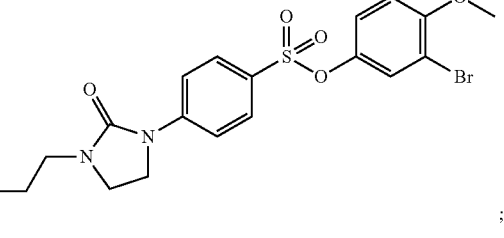
;
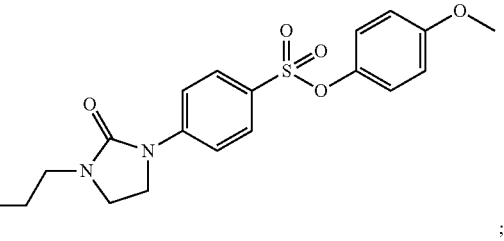
;
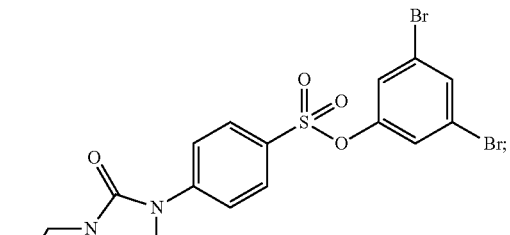
;

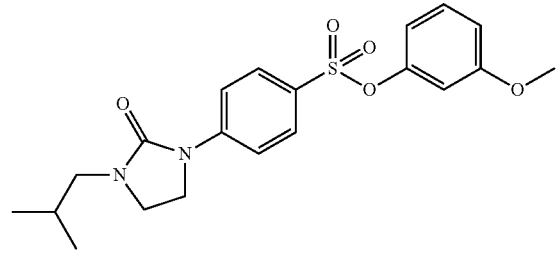
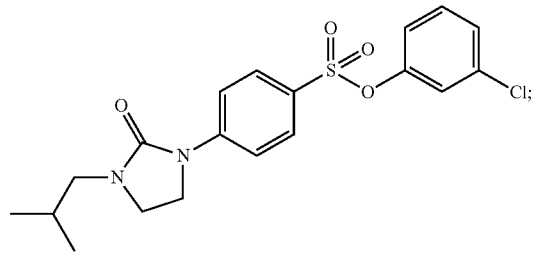
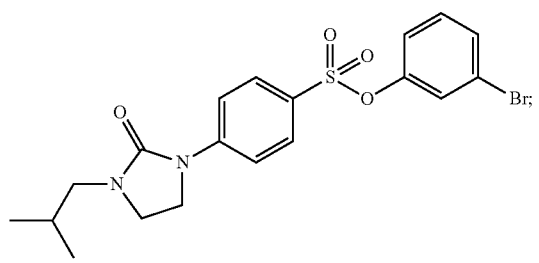
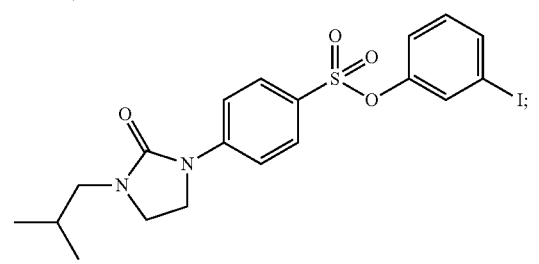
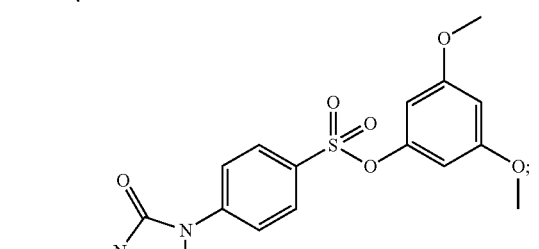
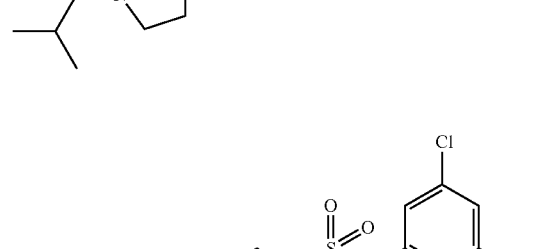
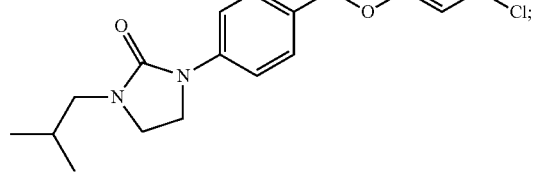
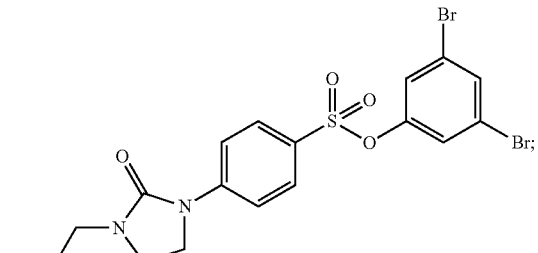
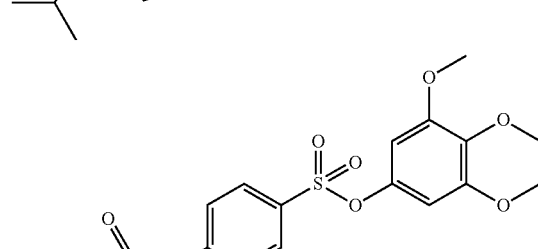
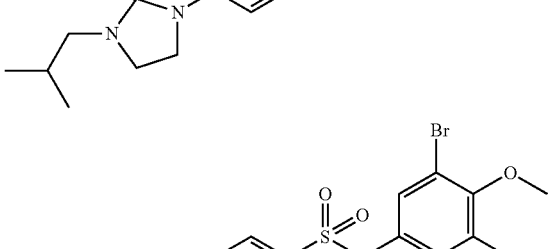
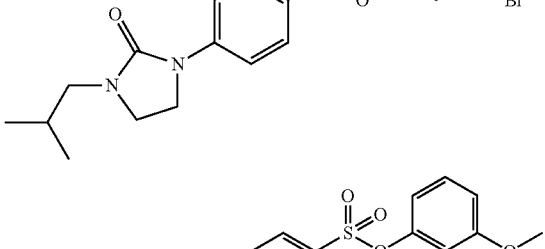
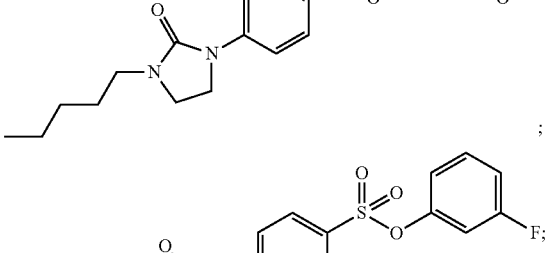
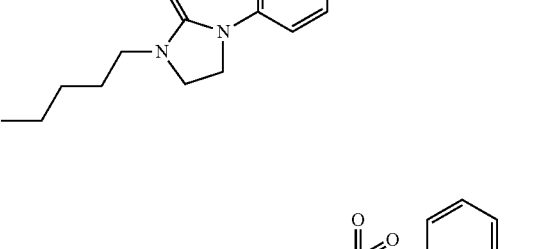
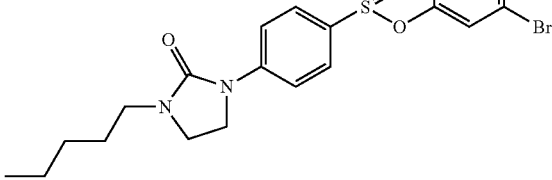

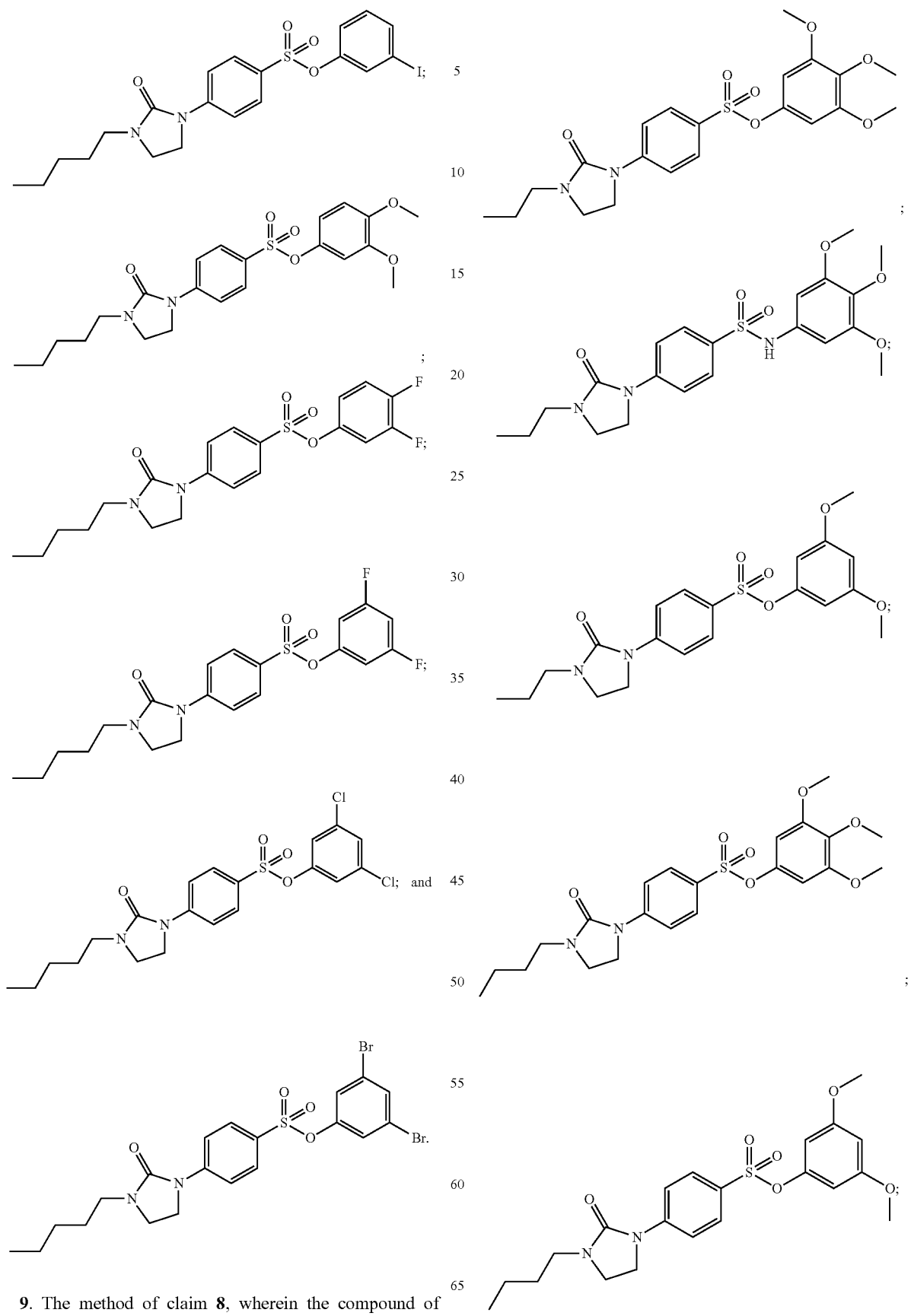
9. The method of claim 8, wherein the compound of formula (Ib) is selected from the group consisting of:

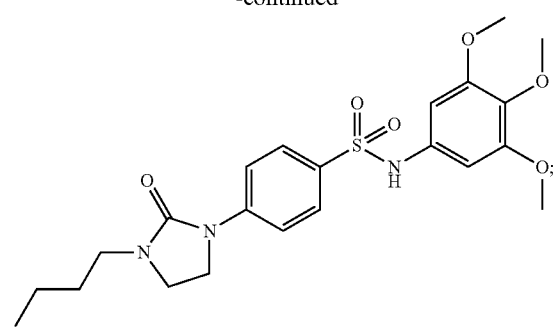
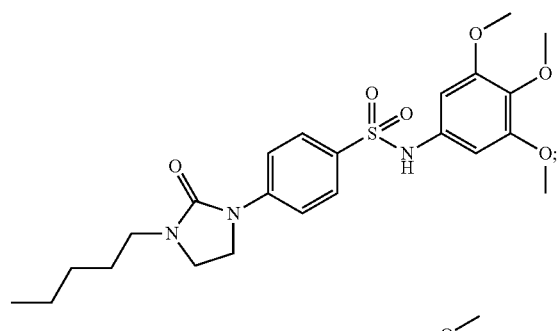
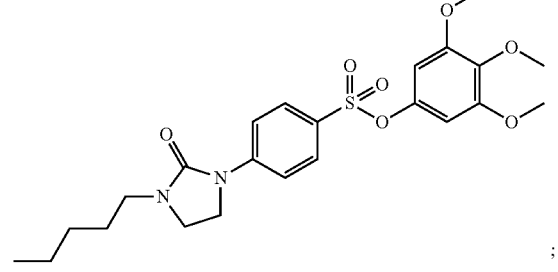
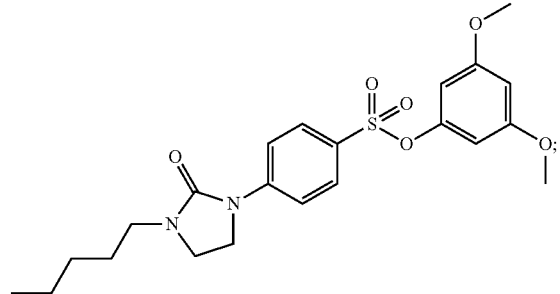
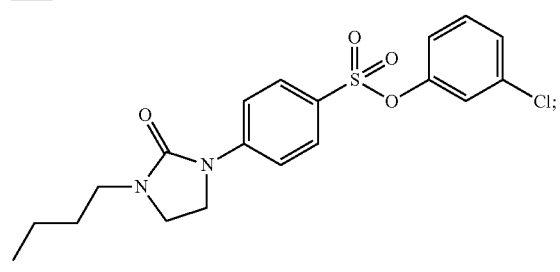
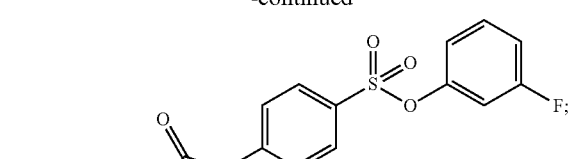
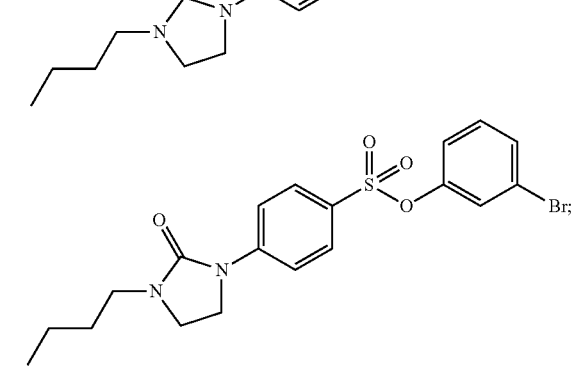
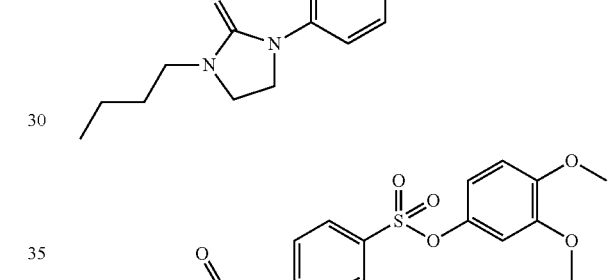
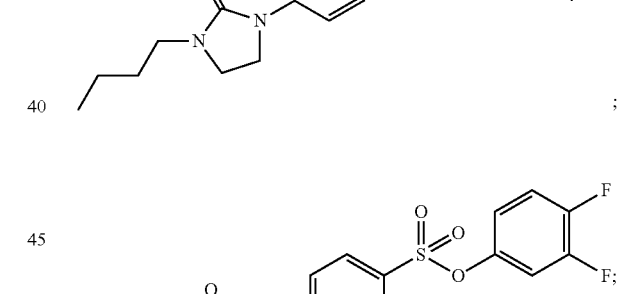
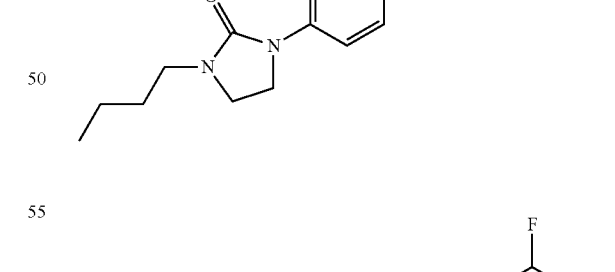
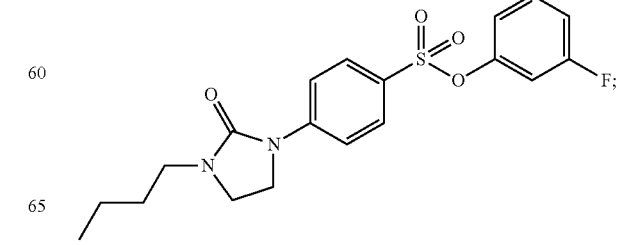

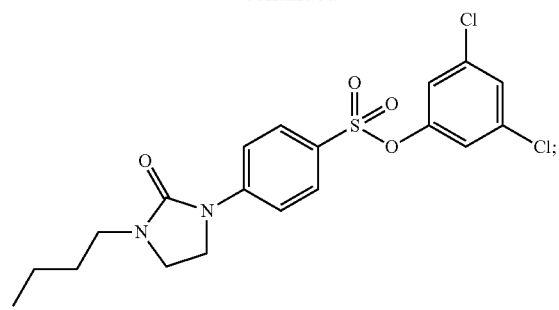
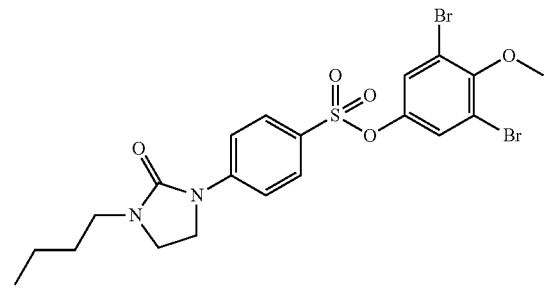
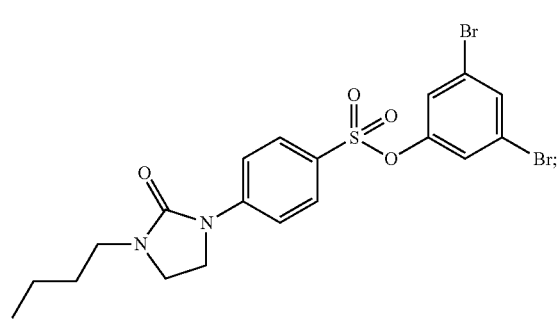
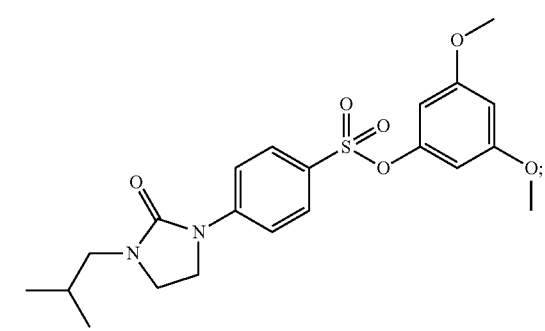
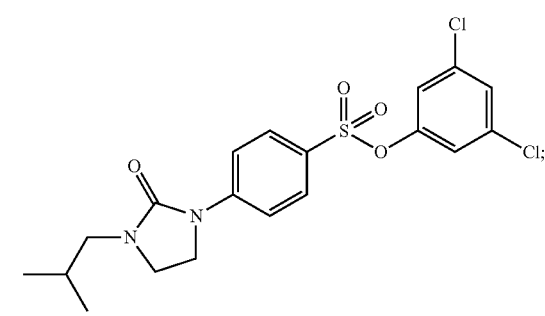
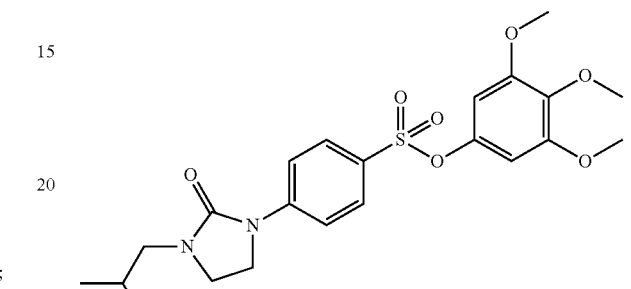
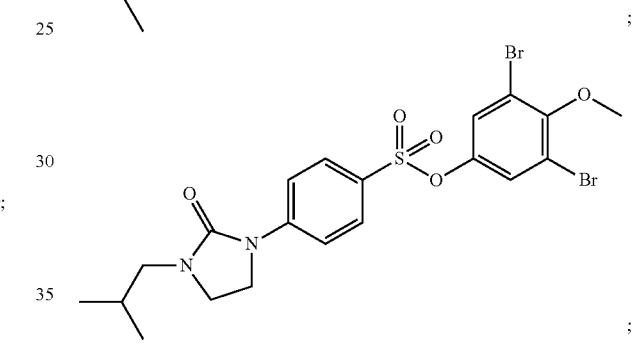
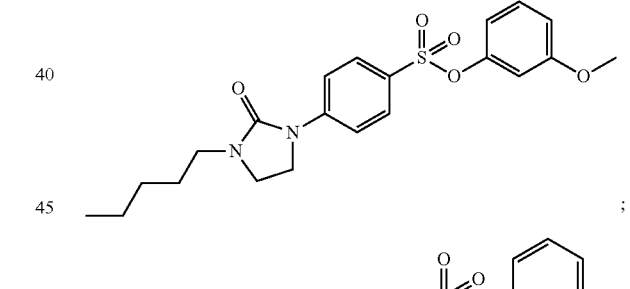
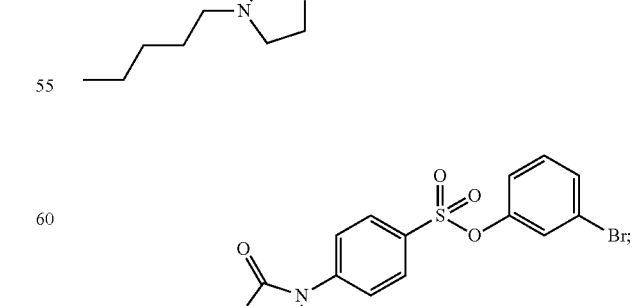

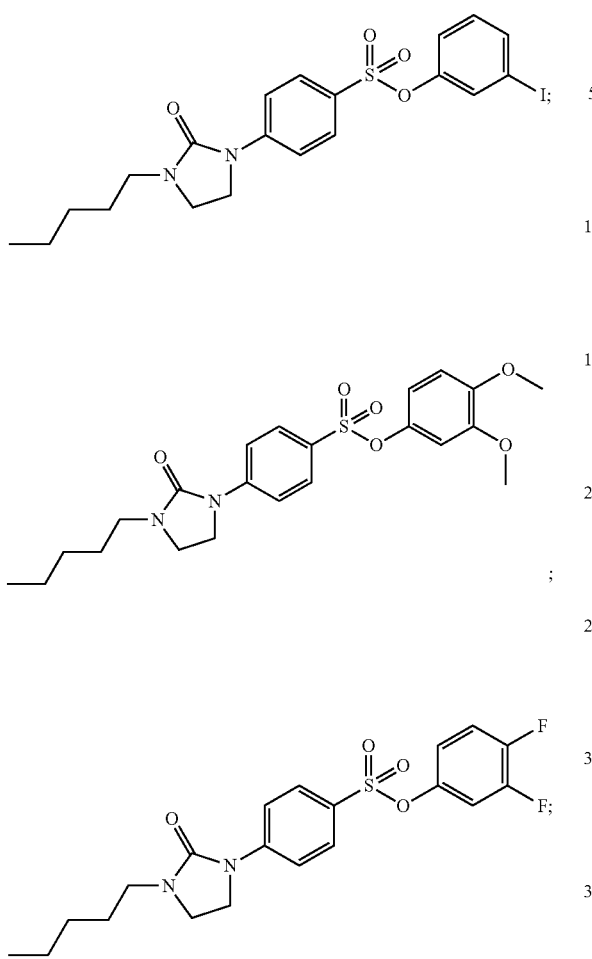
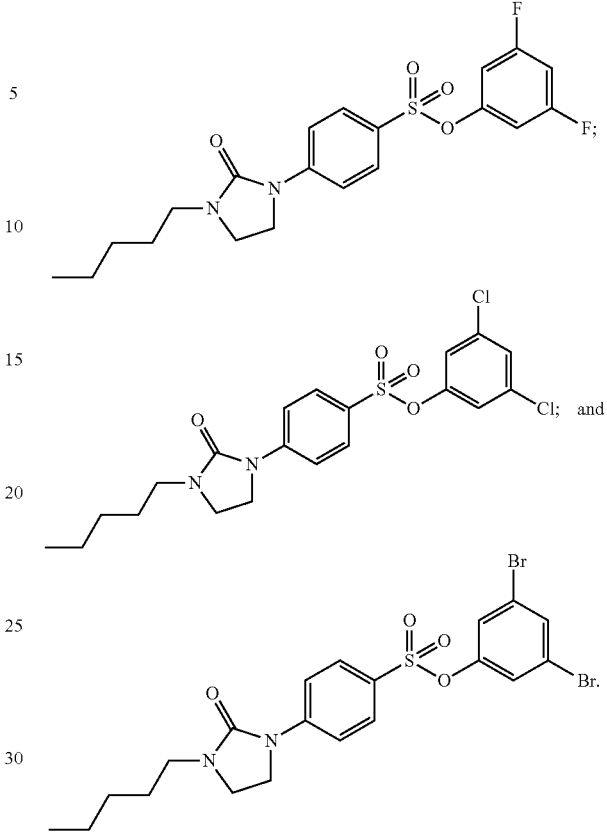
10. The method of claim 1, wherein the cancer is selected from the group consisting of: gastrointestinal cancer and breast cancer.
11. The method of claim 10, wherein the cancer is breast cancer.
* * * * *